(12) United States Patent
Brickl et al.

(10) Patent No.: US 8,598,183 B2
(45) Date of Patent: Dec. 3, 2013

(54) SOLID STATE FORMS OF A POTENT HCV INHIBITOR

(75) Inventors: Rolf-Stefan Brickl, Warthausen (DE); Shirlynn Chen, Somers, NY (US); Jihchin Chung, Princeton Junction, NJ (US); Mayur Suryakant Dudhedia, Brookfield, CT (US); Danping Li, Middlebury, CT (US); Zhi-Hui Lu, Newtown, CT (US); Siddharthya Mujumdar, Auburndale, MA (US); Chitra Telang, Brookfield, CT (US); Richard J. Varsolona, Scotch Plains, NJ (US); Zeren Wang, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 252 days.

(21) Appl. No.: 13/241,551

(22) Filed: Sep. 23, 2011

(65) Prior Publication Data

US 2012/0122887 A1 May 17, 2012

Related U.S. Application Data

(60) Provisional application No. 61/388,242, filed on Sep. 30, 2010.

(51) Int. Cl.
C07D 235/04 (2006.01)

(52) U.S. Cl.
USPC .................................. 514/256; 544/333

(58) Field of Classification Search
USPC ............................. 544/333; 514/256
See application file for complete search history.

(56) References Cited

U.S. PATENT DOCUMENTS

| | | | |
|---|---|---|---|
| 5,821,242 A * | 10/1998 | Colacino et al. | 514/227.2 |
| 7,141,574 B2 | 11/2006 | Beaulieu et al. | |
| 7,576,079 B2 | 8/2009 | Beaulieu et al. | |
| 7,582,770 B2 * | 9/2009 | Tsantrizos et al. | 548/305.1 |
| 7,879,851 B2 | 2/2011 | Tsantrizos et al. | |
| 7,893,084 B2 | 2/2011 | Beaulieu et al. | |
| 8,030,309 B2 | 10/2011 | Tsantrizos et al. | |

FOREIGN PATENT DOCUMENTS

WO 2005080388 A1 9/2005

OTHER PUBLICATIONS

Stahl et al., eds., Handbook of pharmaceutical salts. Properties, selection and use (Wiley-VCH, 2008), pp. 265-327.*
Serajuddin, Advanced Drug Delivery Reviews 59 (2007) 603-616.*
Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Gould, International J. of Therapeutics 33, pp. 201-213 & 217 (1986).*
Swarbrick et al., eds. Encyclopedia of Pharmaceutical Technology 13 (Marcel Dekker, NY 1996) pp. 453-499.*
International Search Report, Form 210, and Written Opinion, Form 237, of PCT/US2011/052869, date of mailing Dec. 5, 2011.

* cited by examiner

*Primary Examiner* — Deepak Rao
(74) *Attorney, Agent, or Firm* — Michael P. Morris; Philip I. Datlow

(57) ABSTRACT

This invention relates to novel sodium salt forms of the following Compound (1), and methods for the preparation thereof, pharmaceutical compositions thereof, and their use in the treatment of Hepatitis C Viral (HCV) infection:

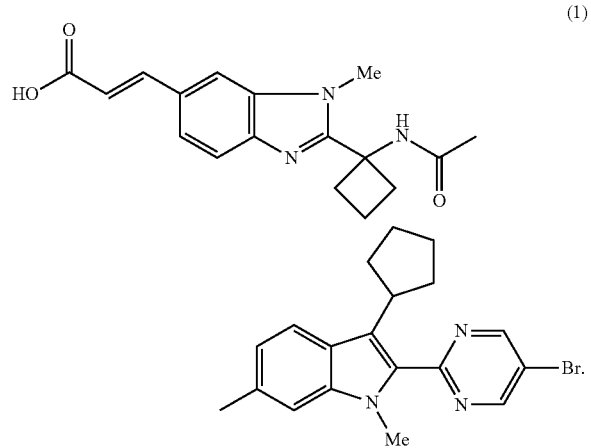

(1)

29 Claims, 11 Drawing Sheets (a) Formulation placebo, (b) Drug substance, and (c) Formulated drug product. Asterisks indicate NMR resonances due to Drug Substance only. NMR resonances with direct overlap between the drug substance and excipients are not marked.

SOLID STATE FORMS OF A POTENT HCV INHIBITOR

FIELD OF THE INVENTION

This invention relates to novel solid state forms of Compound (1), including the crystalline and amorphous forms of the sodium salt of Compound (1) as described herein, methods for the preparation thereof, pharmaceutical compositions thereof, and their use in the treatment of Hepatitis C Viral (HCV) infection.

BACKGROUND OF THE INVENTION

The following Compound (1):

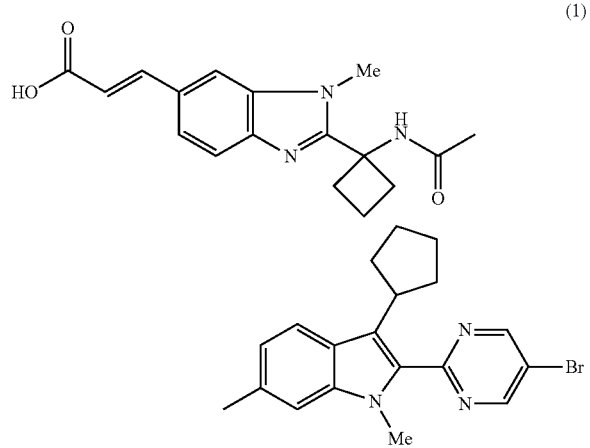

(1)

having the chemical name: (E)-3-[2-(1-{[2-(5-Bromo-pyrimidin-2-yl)-3-cyclopentyl-1-methyl-1H-indole-6-carbonyl]-amino}-cyclobutyl)-3-methyl-3H-benzimidazol-5-yl]-acrylic acid, is known as a selective and potent inhibitor of the HCV NS5B RNA-dependent RNA polymerase and useful in the treatment of HCV infection. Compound (1) falls within the scope of HCV inhibitors disclosed in U.S. Pat. Nos. 7,141,574 and 7,582,770, and US Application Publication 2009/0087409. Compound (1) is disclosed specifically as Compound #3085 in U.S. Pat. No. 7,582,770. Compound (1), and pharmaceutical formulations thereof, can be prepared according to the general procedures found in the above-cited references, all of which are herein incorporated by reference in their entirety. Preferred forms of Compound (1) include the crystalline forms, in particular the crystalline sodium salt form which is prepared as herein described.

When synthesized according to the general procedures set forth in the above-cited references, Compound (1) is prepared as an amorphous solid which is a form that is generally less suitable for full-scale pharmaceutical processing. Thus, there is a need to produce Compound (1) in a form sufficient to enable formulations to meet exacting pharmaceutical requirements and specifications, while providing sufficient in-vivo exposure of the active drug. Furthermore, the process by which Compound (1) is produced needs to be one which is amenable to large-scale production. Additionally, it is desirable that the product should be in a form that is easily processed, e.g. readily filterable and easily dried. Finally, it is economically desirable that the product be stable for extended periods of time without the need for specialized storage conditions.

SUMMARY OF THE INVENTION

We have now found for the first time that Compound (1) can be prepared in the form of its sodium salt, and more preferably the crystalline sodium salt form. This novel crystalline form has unexpectedly superior properties, for example superior dissolution properties and unique solubility characteristics, making it particularly advantageous in pharmaceutical formulation processing as will be described in detail below. Also described is the amorphous sodium salt form having its own unique characteristics that may make it suitable for pharmaceutical processing.

Yet another embodiment is directed to pharmaceutical compositions comprising the crystalline or amorphous Compound (1) sodium salt and at least one pharmaceutically acceptable carrier or diluent.

Yet another embodiment is directed to a method of treating HCV infection in a mammal comprising administering to said mammal a therapeutically effective amount of the crystalline or amorphous Compound (1) sodium salt.

DETAILED DESCRIPTION OF THE INVENTION

Definitions

Figure 1:
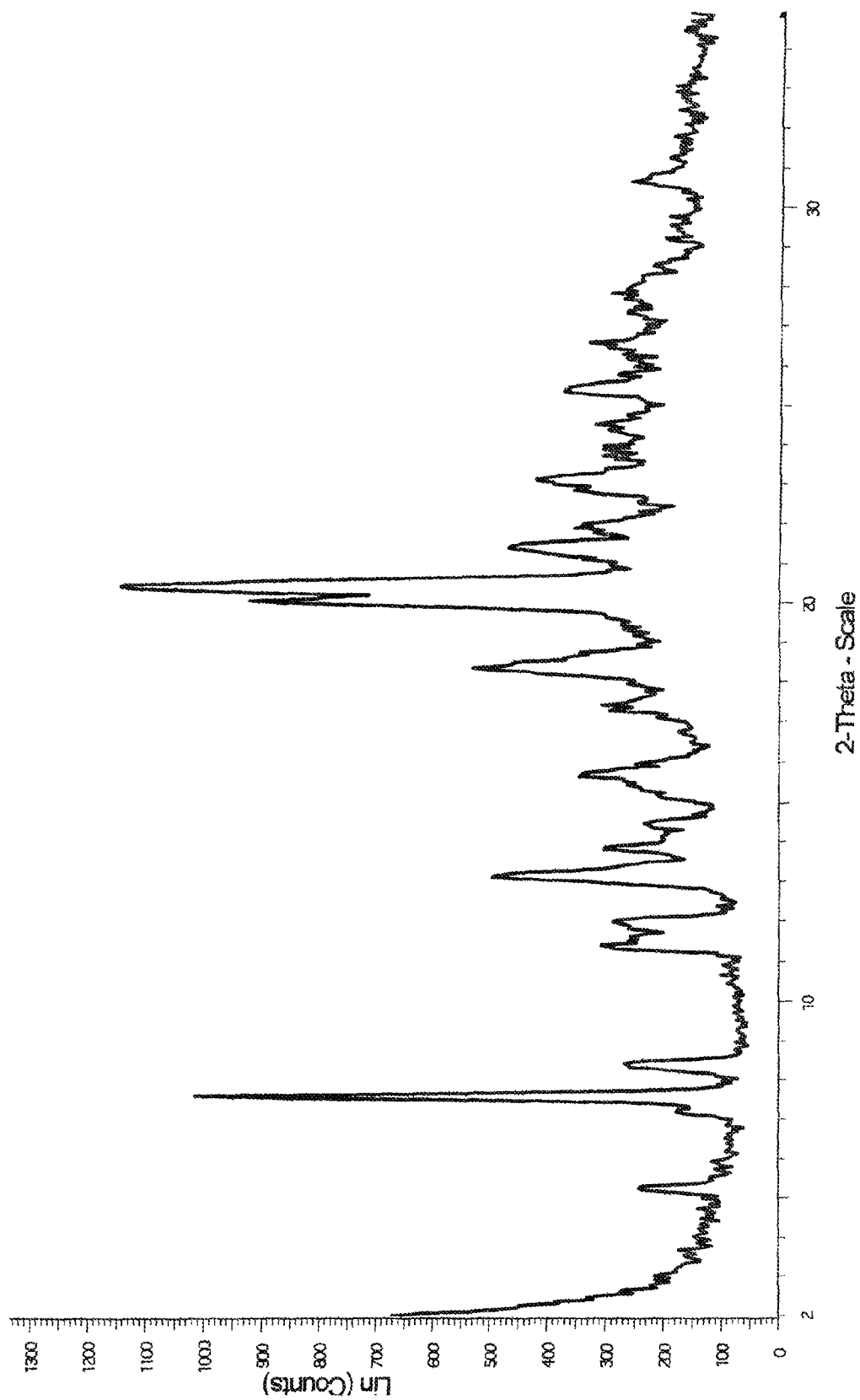
FIG. 1 is a characteristic X-ray Powder Diffraction (XRPD) pattern for the crystalline sodium salt of Compound (1).

Terms not specifically defined herein should be given the meanings that would be given to them by one of skill in the art in light of the disclosure and the context. As used throughout the present application, however, unless specified to the contrary, the following terms have the meaning indicated:

The term "about" means within 5%, and more preferably within 1% of a given value or range. For example, "about 3.7%" means from 3.5 to 3.9%, preferably from 3.66 to 3.74%. When the term "about" is associated with a range of values, e.g., "about X % to Y %", the term "about" is intended to modify both the lower (X) and upper (Y) values of the recited range. For example, "about 20% to 40%" is equivalent to "about 20% to about 40%".

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

Sodium Salt of Compound (1)

Compound (1) is a poorly soluble compound with solubility less than 0.2 μg/mL in physiological pH range of 2-6.8. Doses of Compound (1) up to 400 to 600 mg per dose may be required to be delivered to obtain exposures necessary for sufficient efficacy in vivo.

The Compound (1) active drug moiety has both acid and basic functional groups which lends itself to salt formation. In general, the conversion of the free form to salt form is known to aid solubilization of poorly water soluble drug substances. Multiple pharmaceutically acceptable acid and basic salt forms of Compound (1), including the sodium salt, were produced via crystallization. Significant improvement in the in-vitro dissolution characteristics of the crystalline sodium salt compared to the free acid form and other crystalline salt forms has been demonstrated. This dissolution benefit is expected to translate into improved in vivo exposure of the active drug substance. The crystalline sodium salt form is also preferred because it provides adequate solid state stability and is safe from a toxicological standpoint, which is an important factor to consider for using a high dosing compound such as Compound (1).

The Compound (1) sodium salt can be prepared in either crystalline or amorphous forms or as mixtures thereof, with the crystalline form being preferred. As further described below, different polymorphic forms of the crystalline sodium salt are also possible.

Crystalline Sodium Salt Form

A polymorph screen for Compound (1) sodium salt was conducted using 30 solvents, 24 of them resulted in isolated solids, among which 19 were slurries and 5 were crystallizations. The major polymorphic form was Type A, which was found to have superior properties making it particularly suitable for pharmaceutical development. Other polymorphic forms were discovered but these were found to have certain undesirable properties making them less preferred. Therefore, only Type A Compound (1) sodium salt was chosen for further development and is the specific crystalline sodium salt form that was prepared and characterized as described herein.

The present invention provides a process for the preparation of crystalline sodium salt of Compound (1) which comprises crystallizing Compound (1) from a solution in solvents under conditions which yield crystalline sodium salt. The precise conditions under which crystalline sodium salt is formed may be empirically determined and it is only possible to give methods which have been found to be suitable in practice, as described hereinbelow.

One example of a process that has been found suitable to prepare Type A crystalline sodium salt is as follows:
(a) Reacting Compound (1) with an aqueous NaOH solution in a suitable solvent, such as THF, at ambient temperature to form a clear solution;
(b) Adding methyl ethylketone (MEK, 2 volume per gram of 1) to the mixture obtained in step (a) while heating the mixture to a temperature of about 50-60° C.;
(c) Optionally, adding MEK solvate seeds to the mixture obtained in step (b) at about 50° C.;**
(d) Adding additional MEK (4 volume per gram of 1) to the mixture obtained in step (b) or (c) at about 50° C.
(e) Cooling the mixture obtained in step (d) to about 25° C., resulting in precipitation of Compound (1) sodium salt Type A crystals.
**The Compound (1) sodium salt (Type A) MEK solvate seeds used in the above process step (c) can be manufactured by the above general process except without using seeds and without drying of the solvate.

Specific procedures found to be suitable for preparing crystalline Compound (1) sodium salt, and other characteristics thereof, as well as formulations that may be prepared using the crystalline sodium salt, are as described in the Examples section herein. The prepared crystalline form of Compound (1) sodium salt can either be used directly as it is or subject to an appropriate process to (1) reduce the extent of agglomeration of drug substance particles and/or (2) reduce the particle size distribution of the drug substance primary particles. The process used can be sieving, deagglomeration, impact milling, jet milling or combinations thereof. Details on the use of crystalline Compound (1) sodium salt in various solid dosage formulation compositions are discussed in the Examples section herein.

In one aspect, the present invention is directed to the crystalline sodium salt of Compound (1) (Type A). This crystalline sodium salt of the Compound (1) has been found to be especially suitable for pharmaceutical processing due to the fact that it can be prepared as a stable crystalline form demonstrating superior dissolution properties and unique solubility characteristics.

The crystalline sodium salt has been characterized using X-Ray Powder Diffractometry (XRPD), Solid State NMR (ssNMR), Differential Scanning calorimetry (DSC), and Thermogravimetric Analysis (TGA). Each characterization method and results thereof is described below.

X-Ray Powder Diffractometry (XRPD)

X-ray powder diffraction analyses were conducted on a Bruker AXS X-Ray Powder Diffractometer Model D8 Advance, using CuKα radiation (1.54 Å) in parafocusing mode with a graphite monochromator and a scintillation detector. The pattern was obtained by scanning over a range of 2°-35° 2θ, step size of 0.05° 2θ, step time of 4 sec per step. The XRPD analyses were conducted under ambient laboratory conditions, 25° C./25% RH.

In general, the crystalline sodium salt of Compound (1) (Type A) exhibits a characteristic X-ray powder diffraction (XRPD) pattern with characteristic peaks expressed in degrees 2θ (±0.2 degrees 2θ) at 5.2, 7.5, 8.4, 13.1, 18.3, 20.0, 20.4, 21.4, 23.1 and 25.4.

The XRPD pattern of the crystalline sodium salt of Compound (1) (Type A) is shown in FIG. 1.

In a general embodiment, the present invention is directed to a crystalline sodium salt of Compound (1) that has at least the following characteristic: an X-ray powder diffraction pattern comprising peaks at 7.5 and 20.4 degrees 2θ (±0.2 degrees 2θ) when measured using CuKα radiation. These two XRPD peaks are believed to be sufficient to uniquely identify the presence of the Type A form of Compound (1) sodium salt.

Another embodiment is directed to the crystalline sodium salt of Compound (1) having an XRPD pattern comprising peaks at 7.5, 20.0 and 20.4 degrees 2θ (±0.2 degrees 2θ) when measured using CuKα radiation.

Another embodiment is directed to the crystalline sodium salt of Compound (1) having an XRPD pattern comprising peaks at 7.5, 13.1, 18.3, 20.0, 20.4 and 21.4 degrees 2θ (±0.2 degrees 2θ) when measured using CuKα radiation.

Another embodiment is directed to the crystalline sodium salt of Compound (1) having an XRPD pattern comprising peaks at 5.2, 7.5, 8.4, 13.1, 18.3, 20.0, 20.4, 21.4, 23.1 and 25.4 degrees 2θ (±0.2 degrees 2θ) when measured using CuKα radiation.

The error range of ±0.2 degrees 2θ as stated herein for the various XRPD embodiments applies to all the listed peaks.

Another embodiment is directed to the crystalline sodium salt of Compound (1) exhibiting an XRPD pattern substantially the same as that shown in FIG. 1.

Analyses of crystalline Compound (1) sodium salt (Type A) by XRPD under various relative humidity conditions (dry nitrogen up to ~85% RH) indicate that the crystal lattice expands at higher RH levels while generally maintaining its overall structure and contracts when exposed to ambient conditions. This behavior is typical of channel hydrates, whereby water resides within the channels in the crystal lattice and can readily move in and out of the structure. Crystalline Compound (1) sodium salt is therefore believed to be a type of channel hydrate.

The XRPD pattern of crystalline Compound (1) sodium salt varies slightly with its moisture content in that there is a slight shifting of the pattern at different relative humidity levels. For example, in the range of low RH (about 2%) to high RH (about 85%) the shift of the pattern is about ±0.2 degrees 2θ from the pattern at ambient RH (in general, a low RH results in a positive shift, whereas a high RH results in a negative shift). The XRPD of Type A is therefore defined herein including an "error" range (±0.2 degrees 2θ) believed sufficient to cover the XRPD pattern of crystalline Compound (1) sodium salt at all RH levels. The shift in the XRPD pattern at different RH levels is not exactly consistent throughout the pattern, which would indicate that the crystal lattice is likely expanding more in one dimension than another. The present invention is intended to cover crystalline Compound (1) sodium salt at all RH levels.

The following experiment was conducted to analyze the XRPD shift under variable humidity conditions:

Instrumental Parameters:
Bruker D-8 Advance X-Ray Powder Diffractometer in parallel beam mode with a scintillation detector and using a variable temperature/humidity stage. Humidity adjusted and equilibrated at 25° C., scans from 2-35° 2-theta, 0.05° 2-theta step size, 4 seconds/step As humidity is decreased (dry nitrogen purge) the lines in the resulting diffraction pattern are shifted as compared to the diffraction pattern at ambient conditions. This observation is consistent with lattice contraction due to loss of water. The patterns obtained after 1 hour and after 18 hours with dry nitrogen were consistent and the diffraction pattern at ambient conditions after nitrogen purge is consistent with the initial diffraction pattern.

At higher humidity (50% RH, and 85% RH) the diffraction lines in the resulting patterns are shifted consistent with lattice expansion to accommodate more water in the lattice. The amount of water at 50% RH based on the adsorption curve of the VTI measurement is 1.7%, and the amount of water at 85% RH is 4.5%. When the sample is exposed to ambient conditions after high humidity the resulting diffraction pattern is again consistent with that of the starting material.

Figure 2:
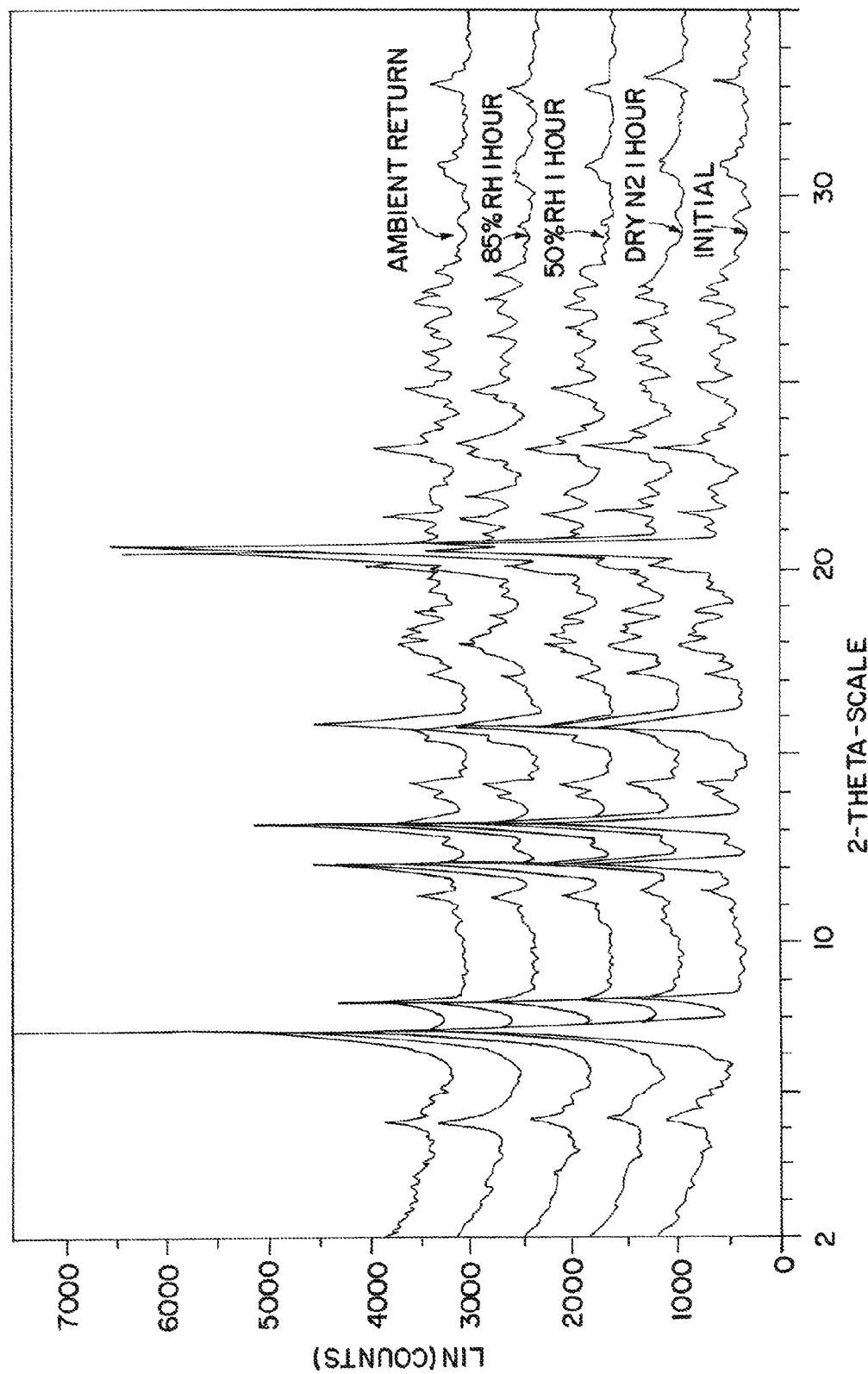
FIG. 2 shows the XRPD diffraction patterns of crystalline Compound (1) sodium salt under different conditions: initial (ambient), dry nitrogen 1 hour, 50% RH, 85% RH and ambient return.

FIG. 2 shows the XRPD diffraction patterns of Compound (1) sodium salt under different conditions: initial (ambient), dry nitrogen 1 hour, 50% RH, 85% RH and ambient return.

Figure 3:
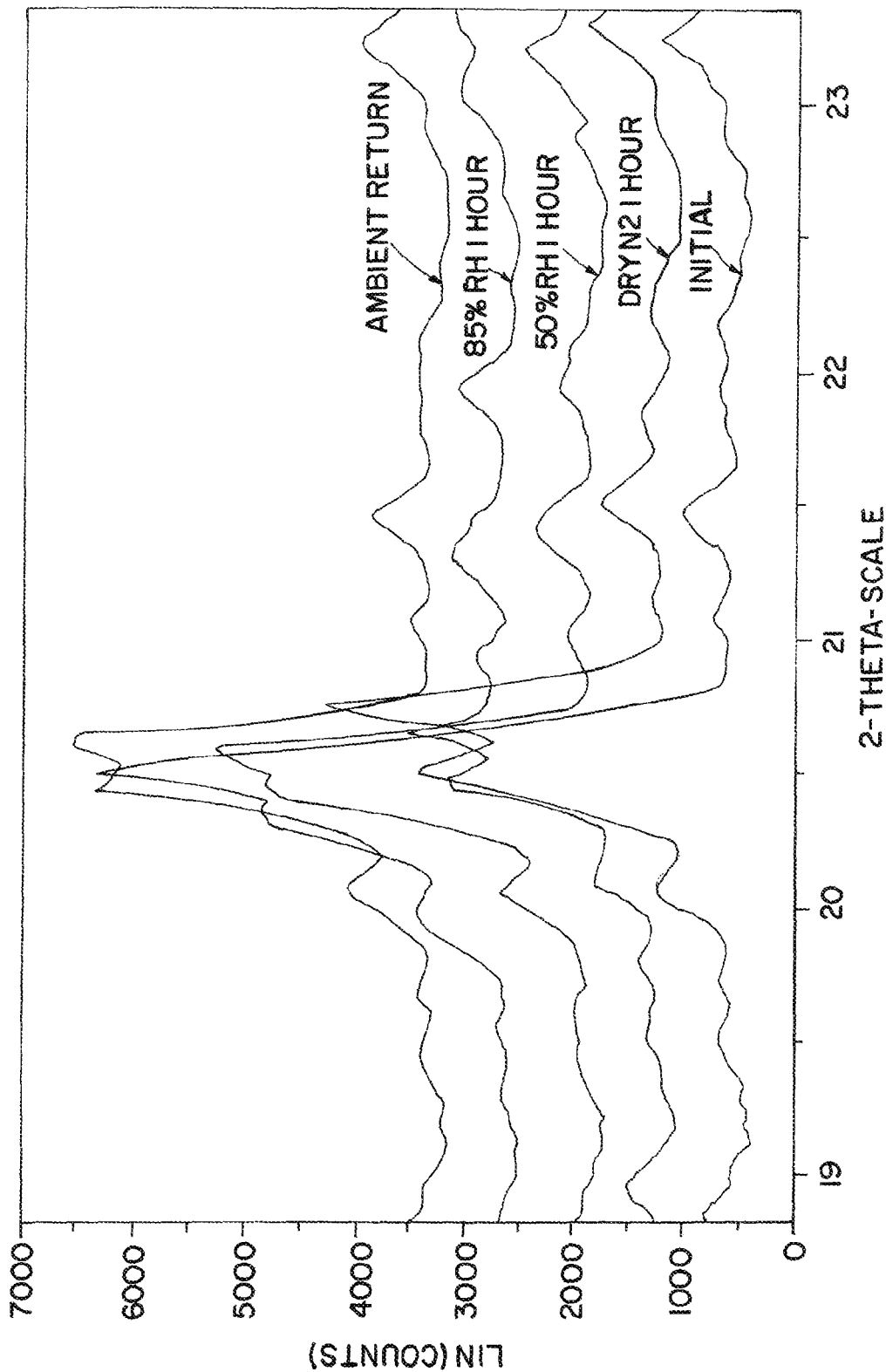
FIG. 3 shows the XRPD diffraction patterns of crystalline Compound (1) sodium salt (from about 18.8 to 23.3 degrees 2θ) under different conditions: initial (ambient), dry nitrogen 1 hour, 50% RH, 85% RH and ambient return.

FIG. 3 shows the XRPD diffraction patterns of Compound (1) sodium salt (from about 18.8 to 23.3 degrees 2θ) under different conditions: initial (ambient), dry nitrogen 1 hour, 50% RH, 85% RH and ambient return.

Figure 4:
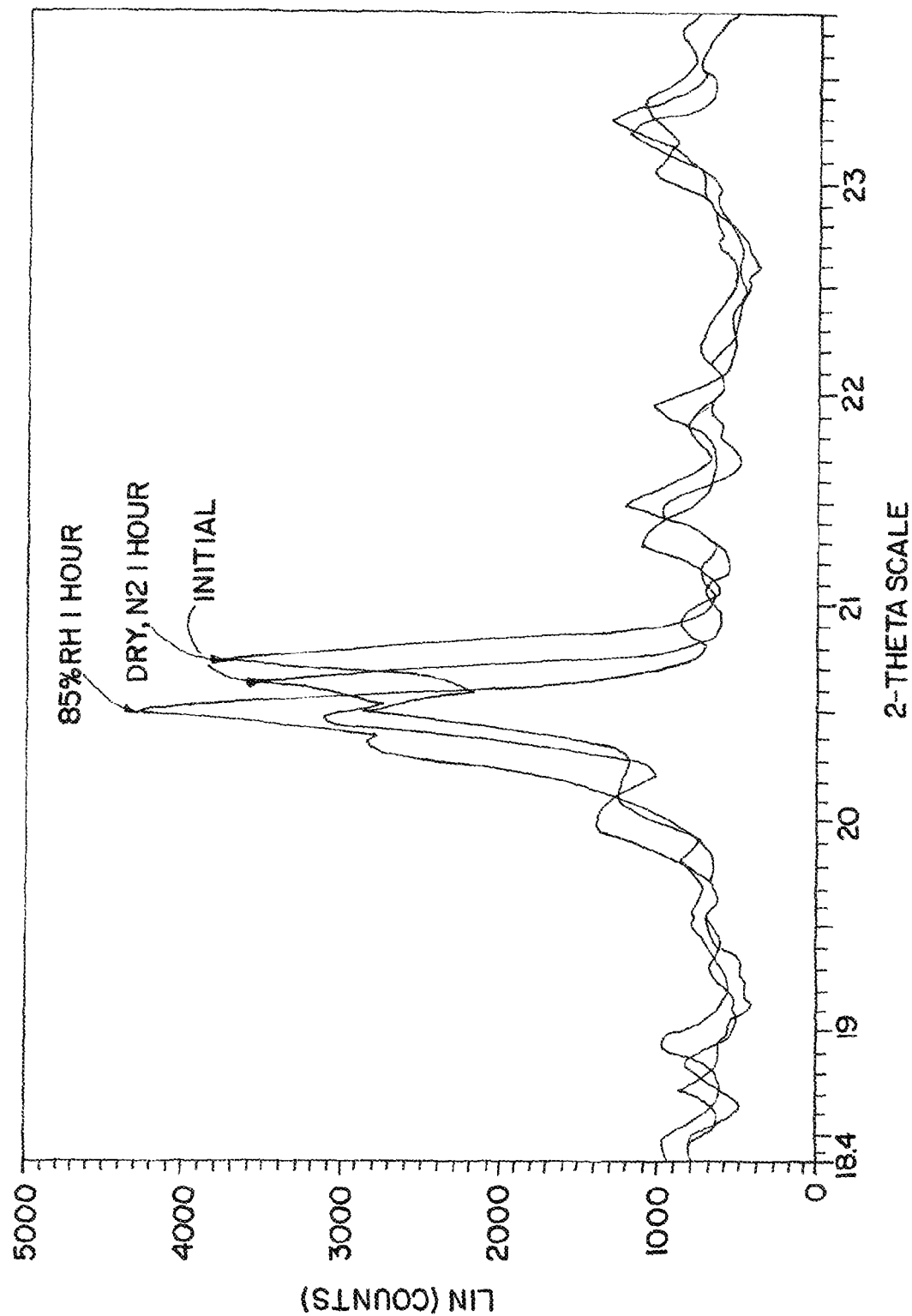
FIG. 4 shows the XRPD diffraction patterns of crystalline Compound (1) sodium salt (from about 18.4 to 23.8 degrees 2θ) under different conditions: initial (ambient), dry nitrogen 1 hour and 85% RH.

FIG. 4 shows the XRPD diffraction patterns of Compound (1) sodium salt (from about 18.4 to 23.8 degrees 2θ) under different conditions: initial (ambient), dry nitrogen 1 hour and 85% RH.

Based on the variable humidity XRD experiments and VTI data Compound (1) sodium salt may be classified as a variable (channel) hydrate.

XRPD Analysis of a Dosage Form

To demonstrate the ability of XRPD to identify the crystalline sodium salt of Compound (1) (Type A) in a pharmaceutical dosage form, 400 mg tablets containing Compound (1) Na salt (Type A) were prepared and analyzed by XRPD. A 400 mg tablet was prepared according to Solid Oral Formulation #3 as set forth in Example 4 hereinafter. The tablet was lightly ground for XRPD analysis. X-ray powder diffraction analysis was conducted on a Bruker AXS X-Ray Powder Diffractometer Model D8 Advance, using CuKα radiation (1.54 Å) in parafocusing mode with a graphite monochromator and a scintillation detector. The pattern was obtained by scanning over a range of 2°-35° 2θ, step size of 0.05° 2θ, step time of 4 sec per step.

Figure 5:
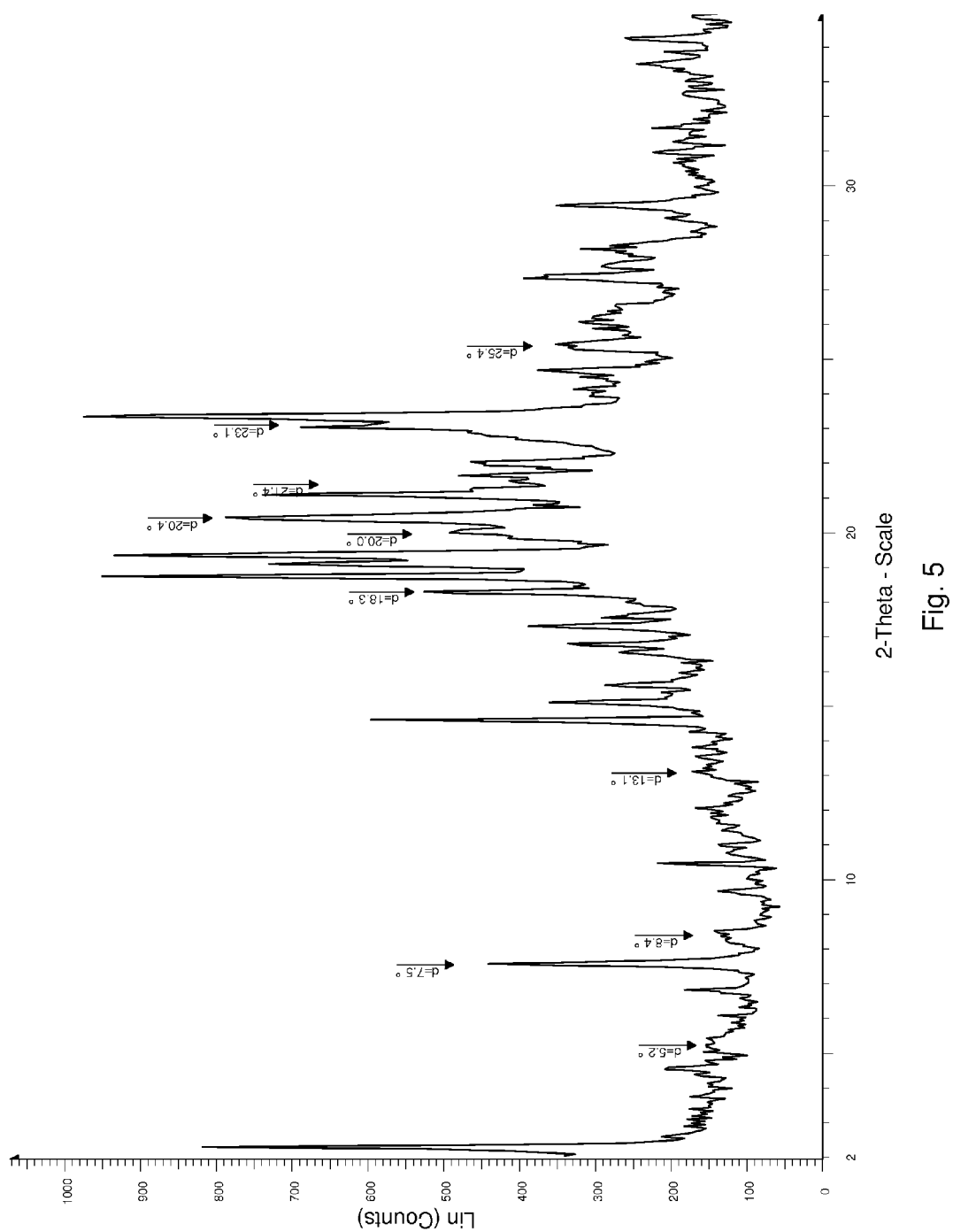
FIG. 5 shows the XRPD diffraction pattern of a tablet containing crystalline Compound (1) sodium salt

A representative XRPD diffraction pattern of the tablet containing Compound (1) Na salt (Type A) is shown in FIG. 5. As can be seen in FIG. 5, the above-mentioned characteristic peaks associated with the API material (Compound (1) Na salt) are clearly discernible in the XRPD pattern of the tablet, although as expected there is a decrease in reflection intensity for various API peaks resulting from a dilution effect due the presence of excipients in the tablet formulation. Nevertheless, the fact that all the original API peaks are discernible is evidence that there is no form change upon formulating the API material.

Solid State NMR (ssNMR)

Solid-state NMR (ssNMR) data was acquired on a Bruker Advance III NMR spectrometer (Bruker Biospin, Inc., Billerica, Mass.) at 9.4 T ($^1H$=400.46 MHz, $^{13}C$=100.70 MHz). Samples were packed in 4 mm O.D. zirconia rotors with Kel-F® drive tips. A Bruker model 4BL CP BB WVT probe was used for data acquisition and sample spinning about the magic-angle (54.74°). Sample spectrum acquisition used a spinning rate of 12 kHz. A standard cross-polarization pulse sequence was used with a ramped Hartman-Hahn match pulse on the proton channel at ambient temperature and pressure. The pulse sequence used a 2 millisecond contact pulse and a 5 second recycle delay. Two-pulse phase modulated (tppm) decoupling was also employed in the pulse sequence. No exponential line broadening was used prior to Fourier transformation of the free incution decay. Chemical shifts were referenced using the secondary standard of adamantane, with the upfield resonance being set to 29.5 ppm. The magic-angle was set using the $^{79}$Br signal from KBr powder at a spinning rate of 5 kHz.

The $^{13}$C chemical shifts for crystalline Compound (1) sodium salt are reported in Table 1 below.

TABLE 1

| Chemical Shift (ppm) (±0.2 ppm) |
| --- |
| 176.8 |
| 168.4 |
| 160.0 |
| 158.4 |
| 157.3 |
| 155.9 |
| 142.5 |
| 138.8 |
| 137.7 |
| 136.7 |
| 134.6 |
| 132.7 |
| 131.8 |
| 130.3 |
| 129.4 |
| 127.7 |
| 126.7 |
| 122.3 |
| 121.2 |
| 119.9 |
| 111.1 |
| 110.1 |
| 108.9 |
| 106.5 |
| 105.1 |
| 56.1 |
| 55.0 |
| 37.7 |
| 32.5 |
| 32.0 |
| 30.4 |
| 28.9 |
| 26.3 |
| 16.0 |

The chemical shifts reported and claimed herein are accurate to within ±0.2 ppm unless otherwise indicated.

Figure 6:
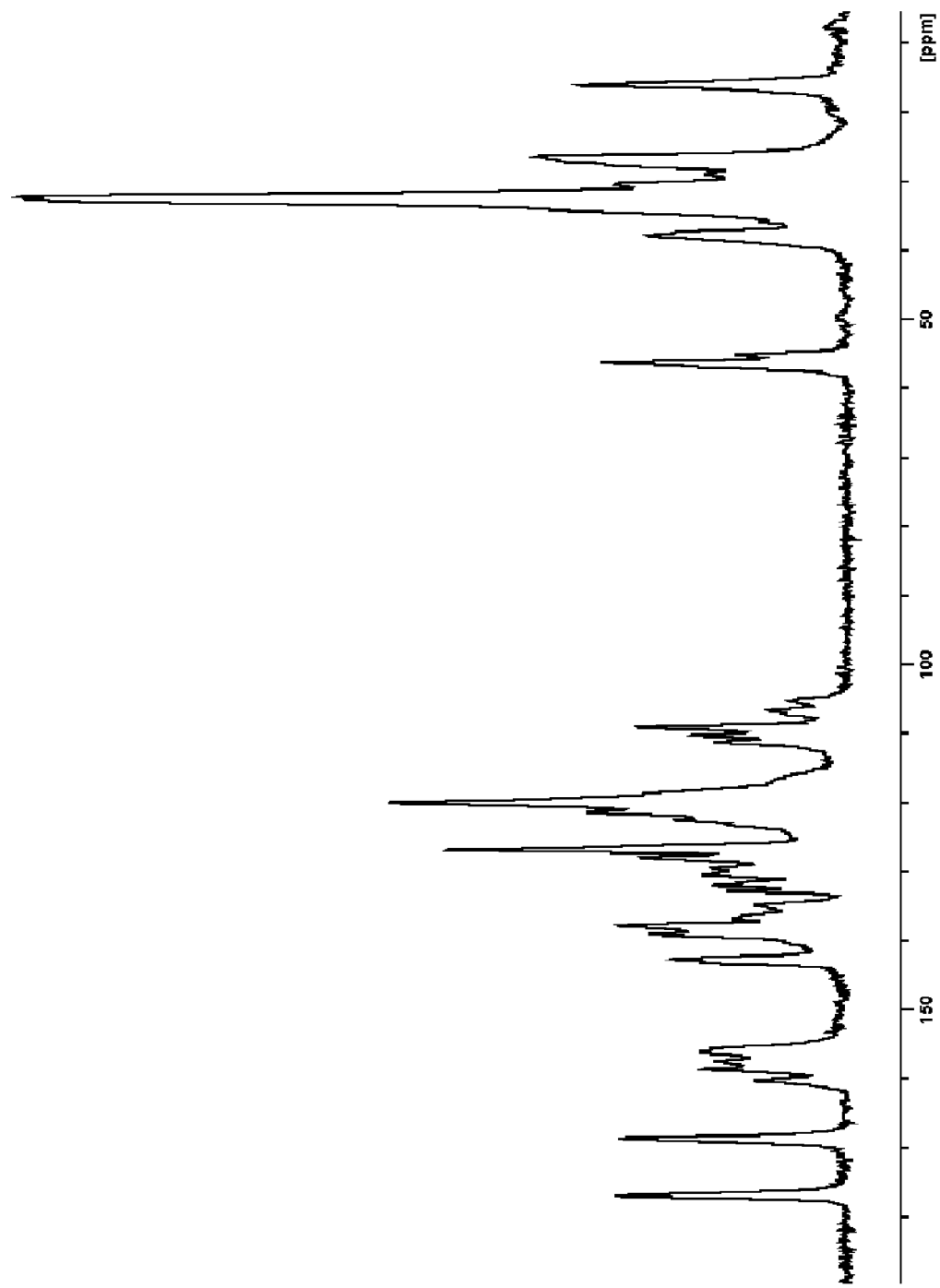
FIG. 6 is a representative $^{13}C$ ssNMR spectrum of Compound (1) sodium salt

A representative $^{13}$C ssNMR spectrum of Compound (1) sodium salt (Type A) is shown in FIG. 6

One general embodiment is directed to a crystalline sodium salt of Compound (1) that has a $^{13}$C solid state NMR spectrum comprising peaks at chemical shifts of 176.8 and 168.4 ppm (±0.2 ppm). These two NMR peaks are believed to be sufficient to uniquely identify the presence of the Type A form of Compound (1) sodium salt.

Another embodiment is directed to a crystalline sodium salt of Compound (1) that has a $^{13}$C solid state NMR spectrum comprising peaks at chemical shifts of 176.8, 168.4, and 16.0 ppm (±0.2 ppm).

Another embodiment is directed to a crystalline sodium salt of Compound (1) that has a $^{13}$C solid state NMR spectrum comprising peaks at chemical shifts of 176.8, 168.4, 142.5, 137.7, 126.7, 119.9, 108.9, and 16.0 ppm (±0.2 ppm).

Another embodiment is directed to a crystalline sodium salt of Compound (1) that has a $^{13}$C solid state NMR spectrum comprising peaks at chemical shifts of 176.8, 168.4, 142.5, 137.7, 126.7, 119.9, 108.9, 37.7, and 16.0 ppm (±0.2 ppm).

The error range of ±0.2 ppm as stated herein for the various ssNMR embodiments applies to all the listed peaks.

Another embodiment is directed to the crystalline sodium salt of Compound (1) exhibiting an $^{13}$C ssNMR spectrum substantially the same as that shown in FIG. 6

All of the solid state NMR embodiments and corresponding claimed embodiments as set forth herein represent the solid state NMR of the crystalline sodium salt of Compound (1) when conducted under ambient laboratory conditions (temperature 17-25° C.; relative humidity 30-60%). There is a possibility of a shift in the NMR spectrum with a change in humidity.

ssNMR Analysis of a Dosage Form

To demonstrate the ability of ssNMR to identify the crystalline sodium salt of Compound (1) (Type A) in a pharmaceutical dosage form, 400 mg tablets containing Compound (1) Na salt (Type A) were prepared and analyzed by ssNMR. A 400 mg tablet was prepared according to Solid Oral Formulation #3 as set forth in Example 4 hereinafter. The tablet was gently ground and the powdered sample was analyzed by ssNMR under the same conditions and using the same equipment as outlined above.

Figure 7:
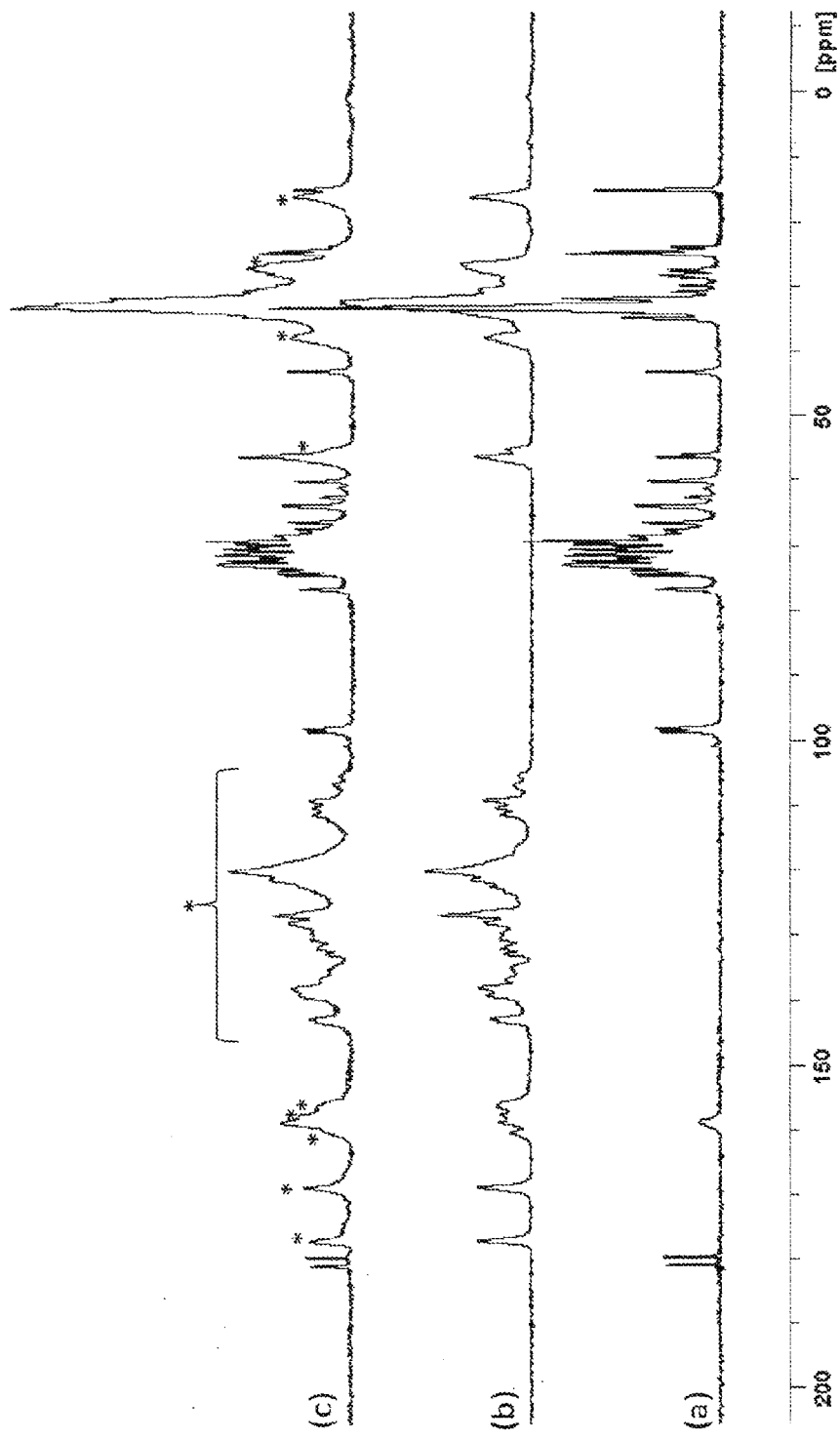
FIG. 7 shows a representative $^{13}C$ ssNMR spectrum of a tablet containing crystalline Compound (1) Na salt (Type A) as spectrum (c) along with a comparison ssNMR plot of the API material alone depicted as spectrum (b) and a comparison ssNMR plot of a formulated placebo tablet as spectrum (a).

FIG. 7 depicts a representative $^{13}$C ssNMR diffraction pattern of the tablet containing Compound (1) Na salt (Type A) as pattern (c), along with a comparison ssNMR plot of the API material depicted as pattern (b) and a comparison ssNMR plot of a formulated placebo tablet as pattern (a). As can be seen in FIG. 7, the above-mentioned characteristic ssNMR peaks associated with the API material (Compound (1) Na salt) are clearly discernible in the ssNMR pattern of the tablet as being clearly associated with the API material. The fact that all the original API peaks are discernible is evidence that there is no form change upon formulating the API material.

Additional XRPD and NMR Embodiments

Additional embodiment are directed to a crystalline sodium salt of Compound (1) having any combination of the above-disclosed XRPD and ssNMR embodiments.

For example, one embodiment is directed to a crystalline sodium salt of Compound (1) having an X-ray powder diffraction pattern comprising peaks at 7.5 and 20.4 degrees 2θ (±0.2 degrees 2θ) when measured using CuKα radiation and a $^{13}$C solid state NMR spectrum comprising peaks at chemical shifts of 176.8 and 168.4 ppm (±0.2 ppm).

In an additional embodiment, the crystalline sodium salt has an X-ray powder diffraction pattern comprising peaks at 7.5, 20.0 and 20.4 degrees 2θ (±0.2 degrees 2θ) when measured using CuKα radiation and having a $^{13}$C solid state NMR spectrum comprising peaks at chemical shifts of 176.8, 168.4 and 16.0 ppm (±0.2 ppm).

In an further additional embodiment, the crystalline sodium salt has an X-ray powder diffraction pattern comprising peaks at 7.5, 13.1, 18.3, 20.0, 20.4 and 21.4 degrees 2θ (±0.2 degrees 2θ) when measured using CuKα radiation and having a $^{13}$C solid state NMR spectrum comprising peaks at chemical shifts of 176.8, 168.4, 142.5, 137.7, 126.7, 119.9, 108.9 and 16.0 ppm (±0.2 ppm).

In an further additional embodiment, the crystalline sodium salt has an X-ray powder diffraction pattern comprising peaks at 5.2, 7.5, 8.4, 13.1, 18.3, 20.0, 20.4, 21.4, 23.1 and 25.4 degrees 2θ (±0.2 degrees 2θ) when measured using CuKα radiation and having a $^{13}$C solid state NMR spectrum comprising peaks at chemical shifts of 176.8, 168.4, 142.5, 137.7, 126.7, 119.9, 108.9, 37.7 and 16.0 ppm (±0.2 ppm).

Additional peak combinations are, of course, possible and are contemplated herein.

Differential Scanning Calorimetry (DSC)

Instrument: TA DSC Q2000 Serial #2000-0794
Sample preparation: Sealed aluminum pan
NB reference 9810-086 N. Taylor
Sample onset of melt is about 326° C. and the peak temperature is about 337° C. A broad thermal event was observed due to the volatilization of the water in the sample (confirmed by Karl Fischer). It should be pointed out that the compound does not purely melt and the endotherm is due to melting with decomposition. The amount of melting with decomposition is based on the compound itself but also sample factors such as particle size, morphology, purity and possibly occluded solvents. We have seen 10 to 15 degree shifts in the observed endotherm during the polymorph screening even though the final solids were all Type A.

Figure 8:
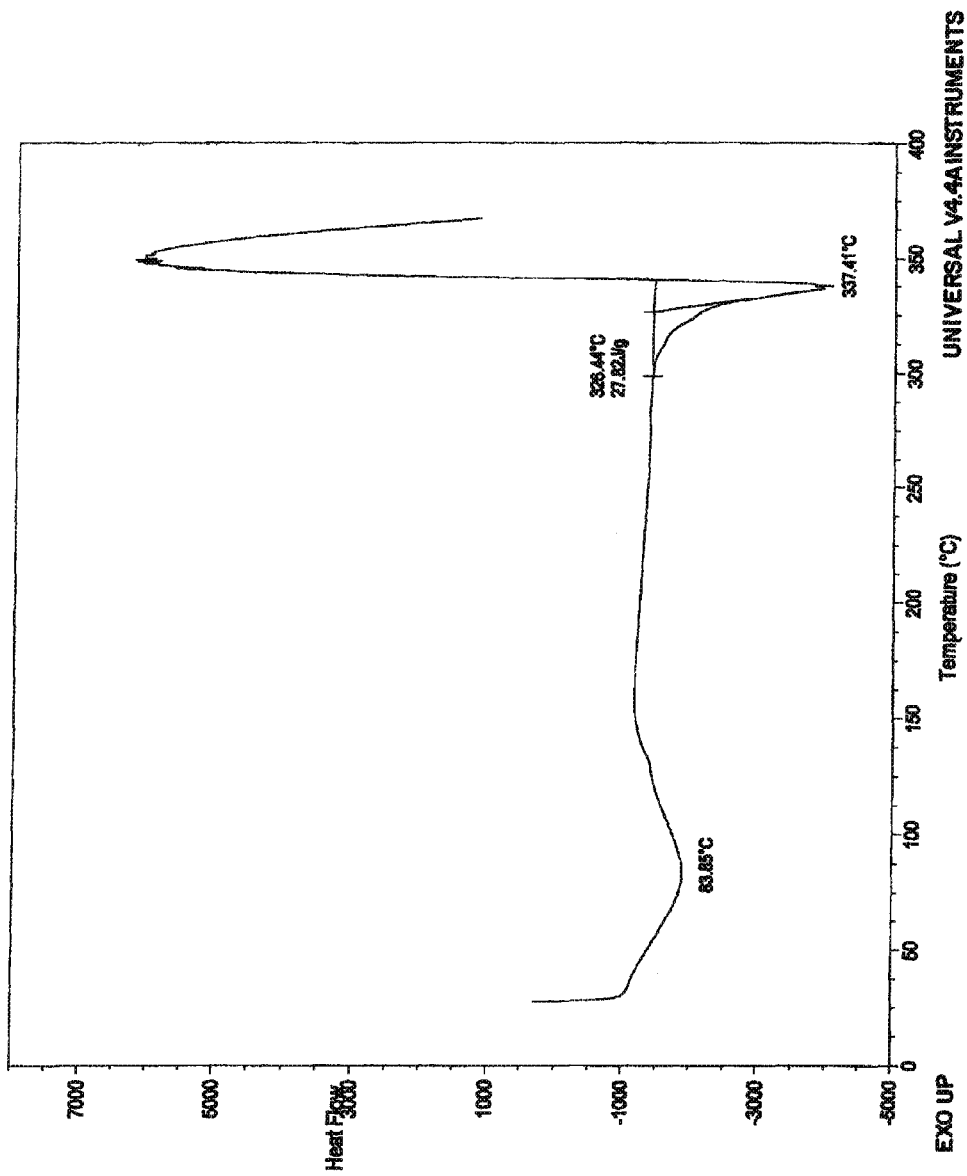
FIG. 8 shows the Differential Scanning calorimetry (DSC) thermal curve for the crystalline sodium salt of Compound (1) (Type A) crystals where the DSC is performed at a heating rate of 10° C. per minute in a sealed aluminum pan.

FIG. 8 shows the Differential Scanning calorimetry (DSC) thermal curve for the crystalline sodium salt of Compound (1) (Type A) crystals where the DSC is performed at a heating rate of 10° C. per minute in a sealed aluminum pan.

Thermogravimetric Analysis (TGA)

Figure 9:
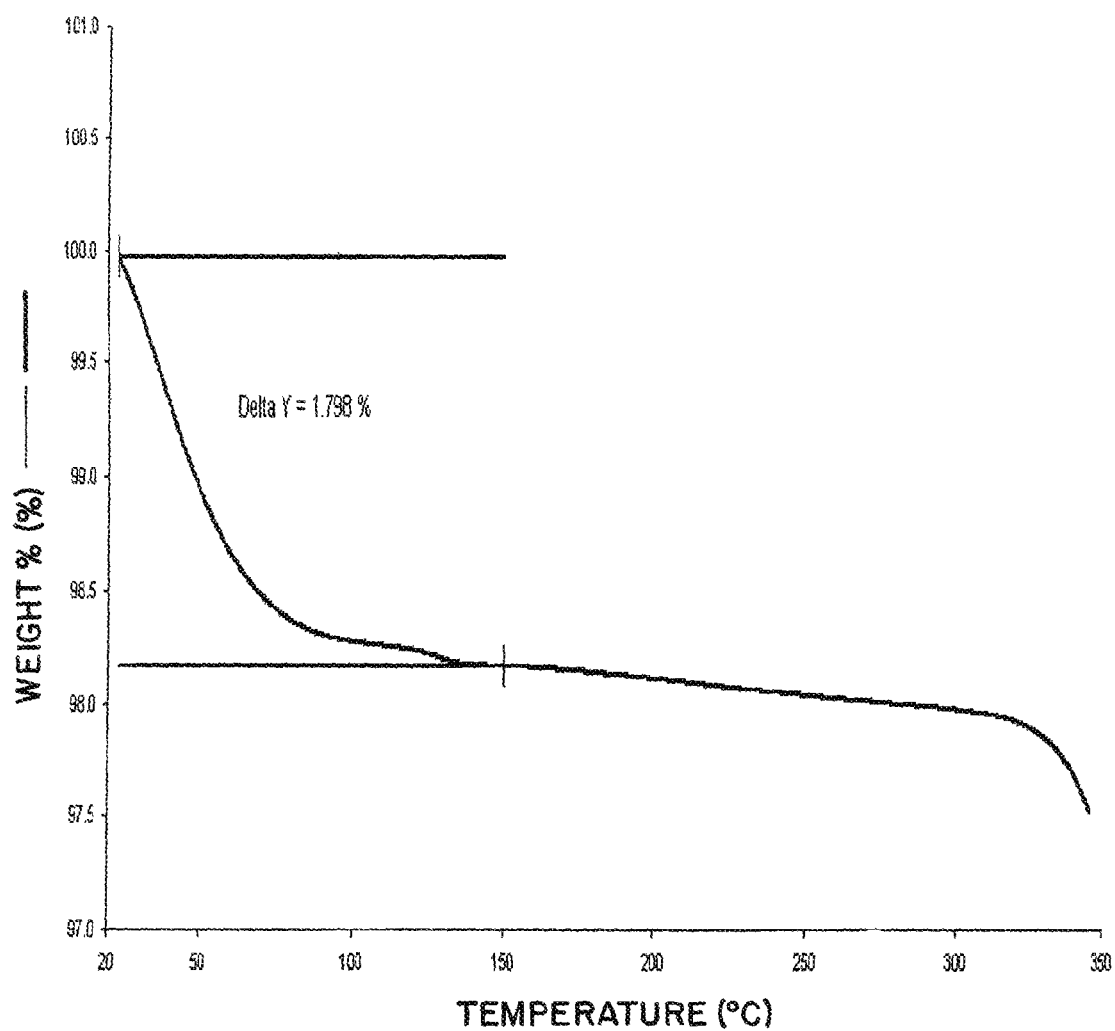
FIG. 9 shows the Thermogravimetric Analysis (TGA) curve for the crystalline sodium salt of Compound (1) (Type A) crystals.

Instrument: Perkin-Elmer TGA 1 Serial #537N 9120103
Conditions: Weight loss calculated from RT to 150° C.
NB reference 9810-085 N. Taylor
FIG. 9 shows the Thermogravimetric Analysis (TGA) curve for the crystalline sodium salt of Compound (1) (Type A) crystals.

Unique Solubilizing Behavior of Compound (1) Na Salt

Based on thermodynamic solubility of Compound (1), solubility of 0.005-0.01 mg/ml is estimated for Compound (1) sodium salt. However, powder dissolution experiments of Compound (1) sodium salt in water indicates that several thousand-fold supersaturation, not found previously with other drugs, can be achieved and maintained for Compound (1) sodium salt in water. Solubility of Compound (1) sodium salt in water at different concentrations is given in Table 2.

TABLE 2

Solubility of Compound (1) sodium salt in water at different concentrations

| conc [mg/ml] | % dissolved |
| --- | --- |
| 0.1 | 13.4 |
| 0.3 | 15.0 |
| 1.0 | 15.4 |
| 3.0 | 46.6 |
| 10.0 | 90.0 |
| 30.0 | 100.0 |
| 100.0 | 100.0 |
| 200.0 | 100.0 |

This unique behavior of high solubility at high drug concentrations is most likely attributable to tendency of the drug substance to self-micellize. A CMC value of 41.4 mM (corresponding to 28 mg/mL) is estimated. At concentrations exceeding the CMC value, Compound (1) sodium salt dissolves completely, whereas at concentrations ≤1 mg/mL only 15% of Compound (1) sodium salt is dissolved. Another surprising observation is that the highly concentrated supersaturated solutions of Compound (1) sodium salt formed are extremely stable with no precipitation observed over 10 month storage at room temperature.

This unique solubilization behavior of Compound (1) sodium salt and the stability of the highly concentrated solutions thereof is a surprising discovery that could not have been predicted beforehand. These unique and unexpected properties of the sodium salt form provide clear benefits in pharmaceutical processing, allowing for the manufacture of stable dosage forms containing high levels of drug product.

The above results obtained with the crystalline sodium salt are unexpected because it is generally not possible to predict such differences in solubility and any trend in physical stability between the free form and different salt forms of a compound even after such forms have been successfully prepared.

Additional Embodiments

Another embodiment is directed to crystalline sodium salt of Compound (1), wherein said crystalline sodium salt is substantially pure Type A as defined herein.

The term "substantially pure" when referring to a designated crystalline form of Compound (1) sodium salt means that the designated crystalline form contains less than 20% (by weight) of residual components such as alternate polymorphic or isomorphic crystalline form(s) thereof. It is preferred that a substantially pure form of Compound (1) sodium salt contain less than 10% (by weight) of alternate polymorphic or isomorphic crystalline forms, more preferred is less than 5% (by weight) of alternate polymorphic or isomorphic crystalline forms, and most preferably less than 1% (by weight) of alternate polymorphic or isomorphic crystalline forms.

Another embodiment is therefore directed to crystalline sodium salt of Compound (1) being in substantially pure Type A form, i.e., wherein at least 80%, preferably at least 90%, more preferably at least 95%, more preferably at least 99%, of said substance is present in the form of Type A crystalline sodium salt of Compound (1), as may be characterized by any of the abovementioned XRPD or ssNMR embodiments.

An additional embodiment is directed to a pharmaceutical composition comprising crystalline Compound (1) sodium salt and at least one pharmaceutically acceptable carrier or diluent. In a more specific embodiment, the crystalline Compound (1) sodium salt in the pharmaceutical composition is as defined by any of the above-mentioned XRPD and/or ssNMR embodiments. In further specific embodiment, the crystalline Compound (1) sodium salt is substantially pure Type A as defined by any of the above-mentioned XRPD and/or ssNMR embodiments. That is, at least 80%, preferably at least 90%, more preferably at least 95%, more preferably at least 99%, of the Compound (1) sodium salt in the composition is present in Type A crystalline form, as characterized by any of the above-mentioned XRPD and/or ssNMR embodiments.

The XRPD and/or ssNMR characterization methods set forth herein can be used to quantify the relative amounts of the preferred crystalline sodium salt form of Compound (1) present in the material.

Pharmaceutical Compositions and Methods

The sodium salt forms of Compound (1), including both the crystalline and amorphous forms described herein, are useful as anti-HCV agents in view of the demonstrated inhibitory activity of Compound (1) against HCV NS5B RNA-dependent RNA polymerase. This form is therefore useful in treatment of HCV infection in a mammal and can be used for the preparation of a pharmaceutical composition for treating an HCV infection or alleviating one or more symptoms thereof in a patient. In addition, the sodium salt form of Compound (1) has demonstrated effectiveness in treating HCV-infected patients in human clinical trials. The appropriate dosage amounts and regimens for a particular patient can be determined by methods known in the art and by reference to the disclosure in U.S. Pat. Nos. 7,141,574 and 7,582,770, and US Application Publication 2009/0087409. Generally, a therapeutically effective amount for the treatment of HCV infection in the mammal is administered. In one embodiment, about 1200 mg to 1800 mg is administered per adult human per day in single or multiple doses.

Specific optimal dosage and treatment regimens for any particular patient will of course depend upon a variety of factors, including the age, body weight, general health status, sex, diet, time of administration, rate of excretion, drug combination, the severity and course of the infection, the patient's disposition to the infection and the judgment of the treating physician. In general, the compound is most desirably administered at a concentration level that will generally afford anti-virally effective results without causing any harmful or deleterious side effects.

The sodium salt form of Compound (1) at a selected dosage level is typically administered to the patient via a pharmaceutical composition. See, e.g., the descriptions in U.S. Pat. Nos. 7,141,574 and 7,582,770, and US Application Publication 2009/0087409 for the various types of compositions that may be employed in the present invention. The pharmaceutical composition may be administered orally, parenterally, topically or via an implanted reservoir. The term parenteral as used herein includes subcutaneous, intracutaneous, intravenous, intramuscular, intra-articular, intrasynovial, intrasternal, intrathecal, and intralesional injection or infusion techniques. Oral administration is preferred.

The pharmaceutical compositions of this invention may contain any conventional non-toxic pharmaceutically-acceptable carriers, diluents, adjuvants, excipients or vehicles. In some cases, the pH of the formulation may be adjusted with pharmaceutically acceptable acids, bases or buffers to enhance the stability of the formulated compound or its delivery form.

The pharmaceutical compositions may also be in the form of an oral pharmaceutical composition comprising the crystalline or amorphous sodium salt of Compound (1) and at least one pharmaceutically acceptable carrier or diluent. The oral pharmaceutical compositions may be orally administered in any orally acceptable dosage form including, but not limited to, tablets, capsules (e.g., hard or soft gelatin capsules), including liquid-filled capsules, and aqueous suspensions and solutions. In the case of tablets or extrudates casted into tablets for oral use, carriers which are commonly used include lactose, mannitol, sugars and corn starch. Lubricating agents, such as magnesium stearate, are also typically added. For oral administration in a capsule form, useful diluents include lactose, mannitol, sugars, microcrystalline cellulose and cellulose derivatives and dried corn starch. Examples of soft gelatin capsules that can be used include those disclosed in EP 649651 B1 and U.S. Pat. No. 5,985,321. When aqueous suspensions are administered orally, the active ingredient is combined with emulsifying and suspending agents. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", 19$^{th}$ ed., Mack Publishing Company, Easton, Pa., 1995.

Certainly, when the crystalline sodium salt is formulated in a liquid vehicle, for example, as a liquid solution or suspension for oral administration or by injection, including for example in liquid-filled capsules, the sodium salt loses its crystalline nature. Nevertheless, the final liquid-based pharmaceutical composition contains the novel sodium salt of Compound (1) and it is therefore to be considered a separate embodiment embraced by the present invention. It was only by discovering a method for preparing the sodium salt in a stable crystalline form that the present inventors enabled efficient pharmaceutical processing and pharmaceutical formulation manufacture using the sodium salt form. Therefore, the final pharmaceutical formulation containing the sodium salt form which was thereby enabled by this discovery is considered another aspect and embodiment of the present invention.

Specific examples describing the preparation of various types of solid oral dosage formulations of Compound (1) sodium salt are as set forth below.

In order that this invention is more fully understood, the following examples are set forth. These examples are for the purpose of illustrating embodiments of this invention, and are not to be construed as limiting the scope of the invention in any way. The reactants used in the examples below may be obtained either as described herein, or if not described herein, are themselves either commercially available or may be prepared from commercially available materials by methods known in the art.

Unless otherwise specified, solvents, temperatures, pressures, and other reaction conditions may be readily selected by one of ordinary skill in the art. Typically, reaction progress may be monitored by High Pressure Liquid Chromatography (HPLC), if desired, and intermediates and products may be purified by chromatography on silica gel and/or by recrystallization.

EXAMPLES

Example 1

Preparation of Compound (1) Sodium Salt

Step 1. Synthesis of Isopropyl
3-Cyclopentyl-1-methyl-1H-indole-6-carboxylate

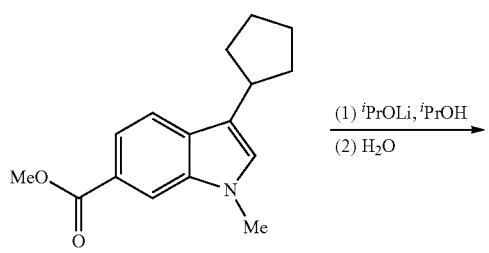

-continued

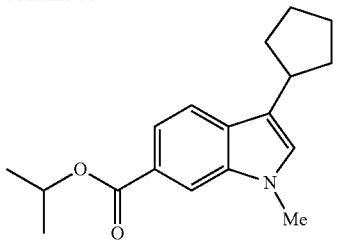

Because of the instability of brominated product, methyl 3-cyclopentyl-1-methyl-1H-indole-6-carboxylate needed to be converted into the more stable isopropyl 3-cyclopentyl-1-methyl-1H-indole-6-carboxylate via a simple and high yielding operation. The conversion worked the best with stoichiometric amounts of solid lithium isopropoxide. Use of 0.1 eq lithium isopropoxide led to longer reaction times and as a result to more hydrolysis by-product, while lithium isopropoxide solution in THF caused a problematic isolation and required distillation of THF.

Procedure:

The mixture of methyl 3-cyclopentyl-1-methyl-1H-indole-6-carboxylate (50.0 g, 0.194 mol) and lithium isopropoxide (16.2 g, 95%, 0.233 mol) in 2-propanol was stirred at 65±5° C. for at least 30 min for complete trans-esterification. The batch was cooled to 40±5° C. and water (600 g) was added at a rate to maintain the batch temperature at 40±5° C. After addition, the mixture was cooled to 20-25° C. over 2±0.5 h and held at 20-25° C. for at least 1 h. The batch was filtered and rinsed with 28 wt % 2-propanol in water (186 g), and water (500 g). The wet cake was dried in vacuo (≤200 Torr) at 40-45° C. until the water content was ≤0.5% to give isopropyl 3-cyclopentyl-1-methyl-1H-indole-6-carboxylate (52.7 g, 95% yield) in 99.2 A % (240 nm).

The starting material methyl 3-cyclopentyl-1-methyl-1H-indole-6-carboxylate can be prepared as described in Example 12 of U.S. Pat. No. 7,141,574, and in Example 12 of U.S. Pat. No. 7,642,352, both herein incorporated by reference.

Step 2. Synthesis of Isopropyl 2-Bromo-3-cyclopentyl-1-methyl-1H-indole-6-carboxylate

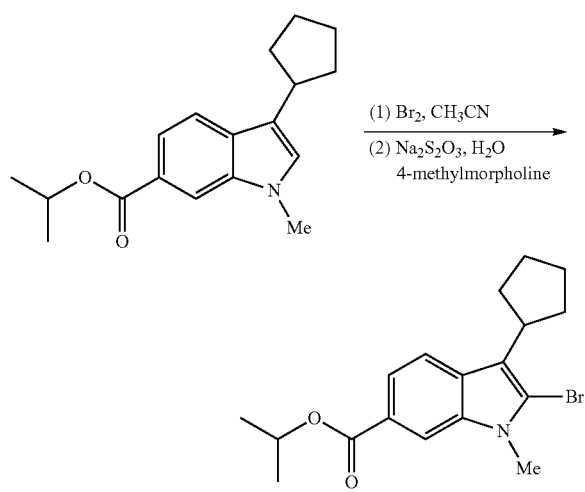

This process identified the optimal conditions for the synthesis of 2-bromo-3-cyclopentyl-1-methyl-1H-indole-6-carboxylate via bromination of the corresponding 3-cyclopentyl-1-methyl-1H-indole-6-carboxylate with bromine. It's very important to control the reaction temperature and to quench the reaction mixture with a mixture of aqueous sodium thiosulfate and 4-methylmorpholine to minimize the formation of the dibromo- and 2-indolone impurities. Further neutralization of the crude product with NaOH in isopropanol greatly increases the stability of the isolated product.

Procedure:

The mixture of isopropyl 3-cyclopentyl-1-methyl-1H-indole-6-carboxylate (50.0 g, 0.175 mol) and acetonitrile (393 g) was cooled to −6±3° C. Bromine (33.6 g, 0.210 mol) was added while the batch was maintained at −6±3° C. The resulting slurry was stirred at −6±3° C. for at least 30 min. When HPLC showed ≥94% conversion (the HPLC sample must be quenched immediately with aqueous 4-methylmorpholine/sodium thiosulfate solution), the mixture was quenched with a solution of sodium thiosulfate (15.3 g) and 28.4 g 4-methylmorpholine in water (440 g) while the temperature was maintained at −5±5° C. After it was stirred at 0±5° C. for at least 2 h, the batch was filtered and rinsed with 85 wt % methanol/water solution (415 g), followed by water (500 g), and dried until water content is ≤30%. The wet cake was suspended in 2-propanol (675 g), and heated to 75±5° C. The resulting hazy solution was treated with 1.0 M aqueous sodium hydroxide solution (9.1 g) and then with 135.0 g water at a rate to maintain the batch at 75±5° C. The suspension was stirred at 75±5° C. for at least 30 min, cooled to 15±2° C. over 30-40 min, and held at 15±2° C. for at least 1 h. The batch was filtered, rinsed with 75 wt % 2-propanol/water solution (161 g), and dried in vacuo (≤200 Torr) at 50-60° C. until the water content was ≤0.4% to give isopropyl 2-bromo-3-cyclopentyl-1-methyl-1H-indole-6-carboxylate as a solid (55.6 g, 87% yield) in 99.5 A % (240 nm) and 97.9 Wt %.

Alternative Procedure:

The mixture of isopropyl 3-cyclopentyl-1-methyl-1H-indole-6-carboxylate (84 g, 0.294 mol) and isopropyl acetate (1074 g) was cooled to between −10-0° C. Bromine (50 g, 0.312 mol) was added while the batch was maintained at −10-0° C. The resulting slurry was stirred at the same temperature for additional 30 min and quenched with a pre-cooled solution of sodium thiosulfate pentahydrate (13 g) and triethylamine (64.5 g) in water (240 g) while the temperature was maintained at 0-10° C. The mixture was heated to 40-50° C. and charged with methanol (664 g). After it was stirred at the same temperature for at least 0.5 h, the batch was cooled to 0-10° C. and stirred for another 1 hr. The precipitate was filtered, rinsed with 56 wt % methanol/water solution (322 g), and dried in vacuo (≤200 Torr) at 50-60° C. until the water content was ≤0.4% to give isopropyl 2-bromo-3-cyclopentyl-1-methyl-1H-indole-6-carboxylate as a beige solid (90-95 g, 80-85% yield).

Step 3a,b. Preparation of Compound I by One-Pot Pd-Catalyzed Borylation-Suzuki Coupling Reaction

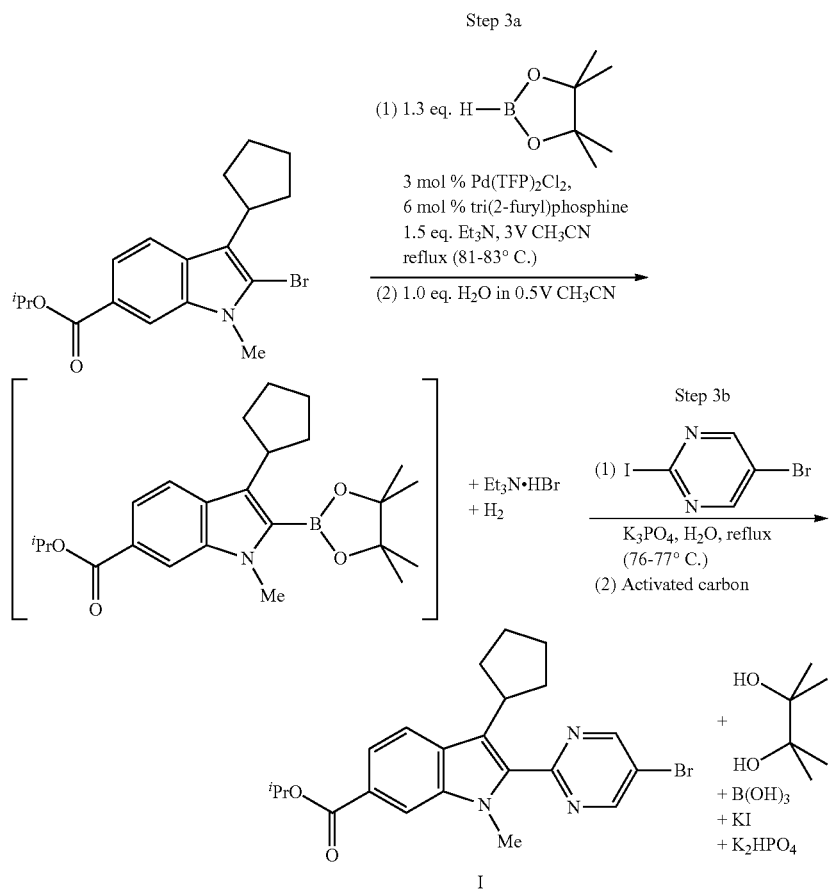

To a clean and dry reactor containing 20.04 g of isopropyl 2-bromo-3-cyclopentyl-1-methyl-1H-indole-6-carboxylate, 1.06 g of Pd(TFP)$_2$Cl$_2$ (3 mol %) and 0.76 g of tri(2-furyl) phosphine (6 mol %) was charged 8.35 g of triethylamine (1.5 equivalent), 39.38 g of CH$_3$CN at 23±10° C. under nitrogen or argon and started agitation for 10 min. 9.24 g of 4,4,5,5-tetramethyl-1,3,2-dioxaborolane was charged into the reactor. The mixture was heated to reflux (ca. 81-83° C.) and stirred for 6 h until the reaction completed. The batch was cooled to 30±5° C. and quenched with a mixture of 0.99 g of water in 7.86 g of CH$_3$CN. 17.24 g of 5-bromo-2-iodopyrimidine and 166.7 g of degassed aqueous potassium phosphate solution (pre-prepared from 46.70 g of K$_3$PO$_4$ and 120 g of H$_2$O) was charged subsequently under argon or nitrogen. The content was heated to reflux (ca. 76-77° C.) for 2 h until the reaction completed. 4.5 g of 1-methylimidazole was charged into the reactor at 70° C. The batch was cooled to 20±3° C. over 0.5 h and hold at 20±3° C. for at least 1 h. The solid was collected by filtration. The wet cake was first rinsed with 62.8 g of 2-propanol, followed by 200 g of H$_2$O. The solid was dried under vacuum at the temperature below 50° C.

Into a dry and clean reactor was charged dried I, 10 wt % Norit SX Ultra and 5 V of THF. The content was heated at 60±5° C. for at least 1 h. After the content was cooled to 35±5° C., the carbon was filtered off and rinsed with 3 V of THF. The filtrate was charged into a clean reactor containing 1-methylimidazole (10 wt % relative to I). After removal of 5 V of THF by distillation, the content was then cooled to 31±2° C. After the agitation rate was adjusted to over 120 rpm, 2.5 V of water was charged over a period of at least 40 minutes while maintaining the content temperature at 31±2° C. After the content was agitated at 31±2° C. for additional 20 min, 9.5 V of water was charged into the reactor over a period of at least 30 minutes at 31±2° C. The batch was then cooled to about 25±3° C. and stirred for additional 30 minutes. The solid was collected and rinsed with 3 V of water. The wet product I was dried under vacuum at the temperature below 50° C. (19.5 g, 95 wt %, 76% yield).

Alternative Procedure:

To a clean and dry reactor containing 40 g of isopropyl 2-bromo-3-cyclopentyl-1-methyl-1H-indole-6-carboxylate (0.110 mol), 0.74 g of Pd(OAc)$_2$ (3.30 mmol, 3 mol % equiv.) and 3.2 g of tri(2-furyl)phosphine (13.78 mmol, 12.5 mol % equiv.) was charged 16.8 g of triethylamine (1.5 equivalent), 100 mL of acetonitrile at 25° C. under nitrogen or argon. 20.8 g of 4,4,5,5-tetramethyl-1,3,2-dioxaborolane was charged into the reactor within 30 min. The mixture was heated to reflux (ca. 81-83° C.) and stirred for over 5 hrs until the reaction completed. The batch was cooled to 20° C. and quenched with a mixture of 2.7 g of water in 50 mL of CH$_3$CN. The batch was warmed to 30° C., stirred for 1 hr and transferred to a second reactor containing 34.4 g of 5-bromo-2-iodopyrimidine in 100 mL of acetonitrile. The reactor was rinsed with 90 mL of acetonitrile. To the second reactor was charged with degassed aqueous potassium phosphate solution (pre-prepared from 93.2 g of K$_3$PO$_4$ and 100 g of H$_2$O)

under argon or nitrogen. The content was heated to reflux (ca. 80° C.) for over 3 h until the reaction completed. 9.2 g of 1-methylimidazole was charged into the reactor at 70° C. and the mixture was stirred for at least 10 min. The aqueous phase was removed after phase separation. 257 g of isopropanol was charged at 70° C. The batch was cooled slowly to 0° C. and hold for at least 1 h. The solid was collected by filtration. The wet cake was rinsed twice with 2-propanol (2×164 g) and dried under vacuum at the temperature below 50° C. to give I as a yellow to brown solid (26 g, 75% yield).

Step 4. Hydrolysis of I to II

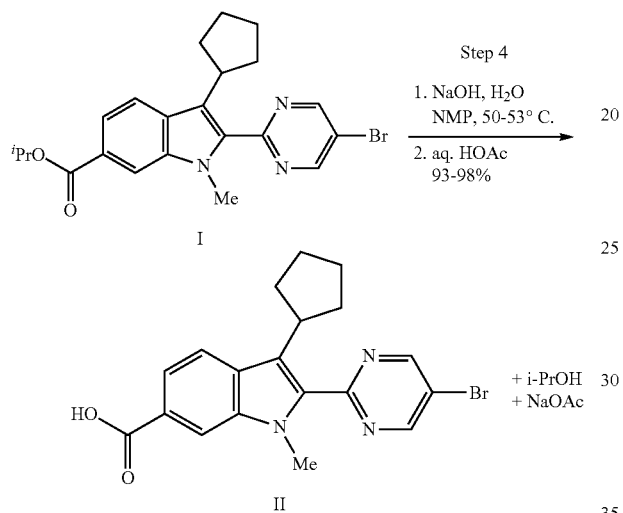

I (20 g) and 1-methyl-2-pyrrolidinone (NMP) (113 g) were charged into a clean reactor under nitrogen. After the batch was heated to 50-53° C. with agitation, premixed aq. NaOH (5.4 g of 50% aq. NaOH and 14.3 g of water) was introduced into the reactor. The resulting mixture was stirred at 50-53° C. for about 10 hrs until the reaction completed. A premixed aq. HOAc (60 g of water and 9.0 g of HOAc) was added over 0.5 h at 45±5° C. to reach pH 5.5-7.5. The batch was cooled to 20±5° C. and then kept for at least 1.0 h. The solid product was collected and rinsed with 80 g of NMP/water (1:3 volume ratio) and then 60 g of water. The product was dried under vacuum at the temperature below 50° C. to give II as a pale yellow powder (19-20 g, purity >99.0 A % and 88.4 wt %, containing 5.4 wt % NMP). The yield is about 93-98%.

Notes: The original procedure used for the hydrolysis of I was carried out with aq. NaOH (2.5 eq) in MeOH/THF at 60° C. Although it has been applied to the preparation of II on several hundred grams scale, one disadvantage of this method is the formation of 5-MeO pyrimidine during hydrolysis (ca. 0.4 A %), which is extremely difficult to remove in the subsequent steps. In addition, careful control has to be exerted during crystallization. Otherwise, a thick slurry might form during acidification with HOAc. The use of NMP as solvent could overcome all aforementioned issues and give the product with desired purity.

Alternative Process

To a reactor was charged I (71 g), isopropanol (332 g), aqueous NaOH (22 g, 45 wt %) and water (140 g) at ambient temperature. The mixture was heated to reflux (80° C.) and stirred for at least 3 hrs until the reaction completed. The batch was cooled to 70° C. and charged a suspension of charcoal (3.7 g) in isopropanol (31 g). The mixture was stirred at the same temperature for over 10 min and filtered. The residue was rinsed with isopropanol (154 g). Water (40 g) was charged to the filtrate at 70-80° C., followed by slow addition of 36% HCl solution (20 g) to reach pH 5-6. The batch was stirred for over 30 min at 70° C., then cooled to 20° C. over 1 hr and kept for at least 1.0 h. The solid product was collected and rinsed with 407 g of isopropanol/water (229 g IPA, 178 g $H_2O$). The product was dried under vacuum at 80° C. for over 5 hrs to give II as a white powder (61 g, 95% yield).

Notes on Steps 5 to 8 Below:

A concise and scalable 4-step process for the preparation of the benzimidazole intermediate V was developed. The first step was the preparation of 4-chloro-2-(methyl)-aminonitrobenzene starting from 2,4-dichloronitrobenzene using aqueous methyl amine in DMSO at 65° C. Then, a ligandless Heck reaction with n-butyl acrylate in the presence of $Pd(OAc)_2$, $^iPr_2NEt$, LiCl, and DMAc at 110° C. was discovered.

Step 5: SNAr Reaction of (5-chloro-2-nitrophenyl)-methylamine

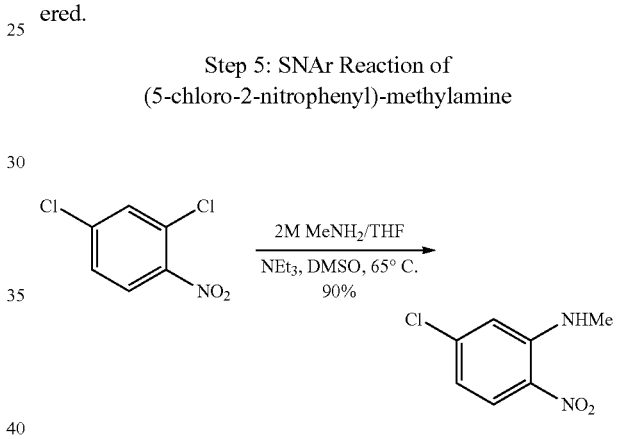

To a solution of (5-chloro-2-nitrophenyl)-methylamine (40 g, 208.3 mmol, 1 equiv) in DMSO (160 mL) was added 40% $MeNH_2$ solution in water (100 mL, 1145.6 mmol, 5.5 eq) slowly keeping the temperature below 35° C. The reaction was stirred at r.t. until the complete consumption of the starting material (>10 h). Water (400 mL) was added to the resulting orange slurry and stirred at r.t. for additional 2 h. The solid was filtered, rinsed with water (200 mL) and dried under reduced pressure at 40° C. (5-chloro-2-nitrophenyl)-methylamine (36.2 g, 93% yield, 94 A % purity) was isolated as a solid.

Step 6: Heck Reaction of (5-chloro-2-nitrophenyl)-methylamine

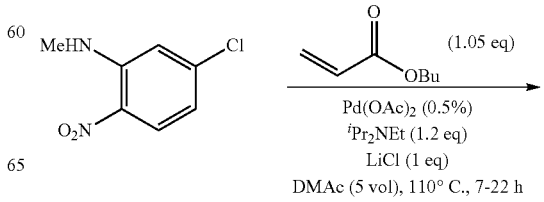

-continued

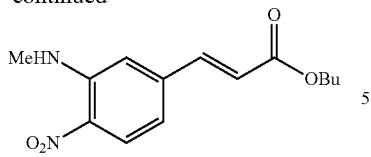

5

To a mixture of 4-chloro-2-methylaminonitrobenzene (50.0 g, 268.0 mmol, 1.0 eq), Pd(OAc)$_2$ (0.30 g, 1.3 mmol, 0.005 eq) and LiCl (11.4 g 268.0 mmol, 1.0 eq) in DMAc (250 mL) was added $^i$Pr$_2$NEt (56 mL, 321.5 mmol, 1.2 eq) followed by n-butyl acrylate (40 mL, 281.4 mmol, 1.05 eq) under nitrogen. The reaction mixture was stirred at 110° C. for 12 h, then cooled to 50° C. 1-methylimidazole (10.6 mL, 134.0 mmol, 0.5 eq) was added and the mixture was stirred for 30 min before filtering and adding water (250 mL). The resulting mixture was cooled to r.t. over 1 h. The resulting solid was filtered and washed with water and dried to yield n-butyl 3-methylamino-4-nitrocinnamate (71.8 g, 96%, 99.2 A % purity).

Step 7: Reduction of n-butyl
(3-methylamino-4-nitro)-cinnamate

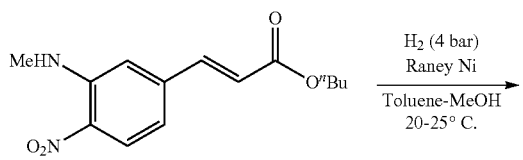

-continued

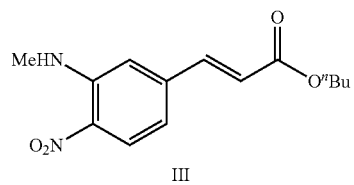

III

To a reactor was charged n-butyl 3-methylamino-4-nitrocinnamate (70.0 g, mmol, 1.0 eq), Raney Ni (4.9 g, ~20 wt % H$_2$O), charcoal "Norit SX Ultra" (3.5 g), toluene (476 mL) and MeOH (224 mL). The reactor was charged with hydrogen (4 bar) and the mixture was stirred at 20-25° C. for about 2 hrs until the reaction was completed. The reaction mixture was filtered and rinsed the filter residue with toluene (70 mL). To the combined filtrates were added "Norit SX Ultra" charcoal (3.5 g). The mixture was stirred at 50° C. for 1.0 hr and filtered. The filtrate was concentrated under reduced pressure to remove solvents to 50% of the original volume. The remained content was heated to 70° C. and charged slowly methyl cyclohexane (335 mL) at the same temperature. The mixture was cooled to about 30-40° C. and seeded with III seed crystals, then slowly cooled the suspension to ~−10° C. The solid was filtered and rinsed with methyl cyclohexane in three portions (3×46 mL). The wet cake was dried in vacuo at 40° C. to give III (53.3 g, 215 mmol, 86%).

Step 8: Preparation of benzimidazole V

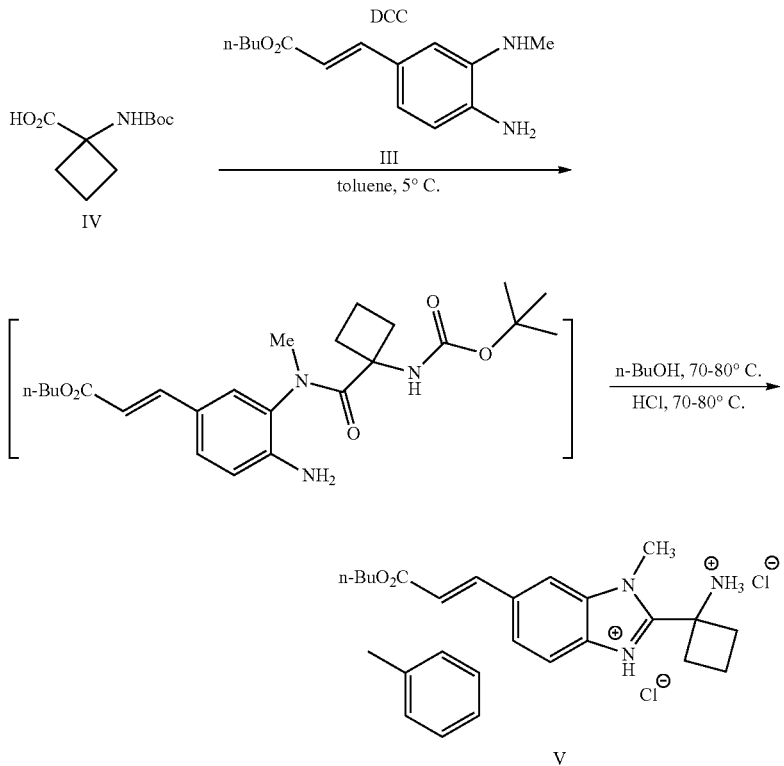

To reactor-1 was charged III (35 g, 140.95 mmol) in toluene (140 g). The mixture was heated to 50° C. to obtain a clear solution. To a second reactor was charged IV (36.4 g, 169.10 mmol) and toluene (300 g), followed by addition of a solution of dicyclohexyl carbodimide (11.6 g, in 50% toluene, 28.11 mmol) at 0-10° C. The mixture was stirred at the same temperature for 15 min, then charged in parallel with the content of reactor-1 and the solution of dicyclohexyl carbodimide (52.4 g, in 50% toluene, 126.98 mmol) within 1 hr while maintaining the batch temperature at 0-10° C. The mixture was agitated at the same temperature for 3 hrs, and warmed to 25° C. for another 1 hr. Once III was consumed, toluene (~300 mL) was distilled off under reduced pressure at 70-80° C. n-Butanol (200 g) was added, followed by 3 M HCl solution in n-butanol (188 g) while maintaining the temperature at 70-80° C. (Gas evolution, product precipitates). After stirring for over 30 min at 70-80° C., the mixture was cooled to 20-30° C. over 1 hr. The precipitate was filtered and washed with acetone (172 g) and toluene (88 g). The wet cake was dried in vacuo at ~60° C. to give V toluene solvate as off white solid (60-72 g, 85-95% yield). Compound V could be used directly for the next step or basified prior to next step to obtain the free base compound VI used in the next step.

Step 9. Synthesis of (E)-Butyl 3-(2-(1-(2-(5-Bromopyrimidin-2-yl)-3-cyclopentyl-1-hydroxy-1H-indole-6-carboxamido)cyclobutyl)-1-methyl-1H-benzo[d]imidazol-6-yl)acrylate VII determined by HPLC (as derivative of diethylamine), the mixture was cooled to 10±5° C. and N,N-diisopropylethylamine (378.77 g, 300 mmol) below 25° C. A solution of (E)-butyl 3-(2-(1-aminocyclobutyl)-1-methyl-1H-benzo[d]imidazol-6-yl)acrylate VI (25.86 g, 97.8 Wt %, 77.25 mmol) dissolved in THF (106.7 g) was added at a rate to maintain the temperature of the content ≤25° C. The mixture was stirred at 25±5° C. for at least 30 min for completion of the amide formation. The mixture was distilled at normal pressure to remove ca. 197 mL (171.5 g) of volatiles (Note: the distillation can also be done under reduced pressure). The batch was adjusted to 40±5° C., and MeOH (118.6 g) was added. Water (15.0 g) was added and the mixture was stirred at 40±5° C. until crystallization occurred (typically in 30 min), and held for another 1 h. Water (90 g) was charged at 40±5° C. over 1 h, and the batch was cooled to 25±5° C. in 0.5 h, and held for at least 1 h. The solid was filtered, rinsed with a mixture of MeOH (39.5 g), water (100 g), and dried in vacuo (≤200 Torr) at 50±5° C. to give (E)-butyl 3-(2-(1-(2-(5-bromopyrimidin-2-yl)-3-cyclopentyl-1-methyl-1H-indole-6-carboxamido)cyclobutyl)-1-methyl-1H-benzo[d]imidazol-6-yl)acrylate VII (51.82 g, 96.6% yield) with a HPLC purity of 98.0 A % (240 nm) and 99.0 Wt %.

Alternative Procedure (Using Compound V from Step 8)
To reactor 1 was charged 2-(5-bromopyrimidin-2-yl)-3-cyclopentyl-1-methyl-1H-indole-6-carboxylic acid II (33.6

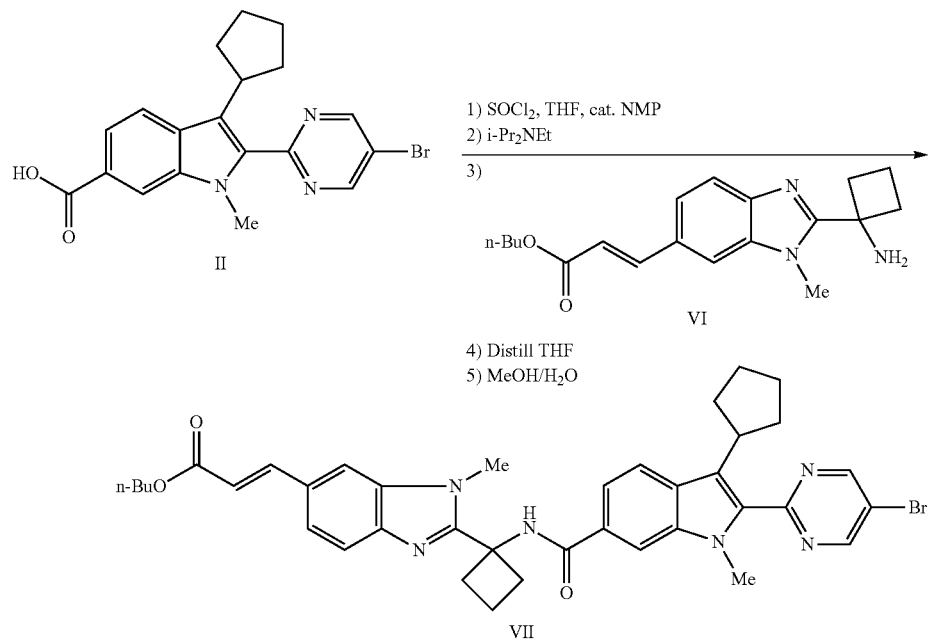

Notes:
The conversion of the acid into acid chloride was achieved using inexpensive thionyl chloride in the presence of catalytic amount of NMP or DMF. An efficient crystallization was developed for the isolation of the desired product in high yield and purity.

Procedure (Using Free Base VI):
To the suspension of 2-(5-bromopyrimidin-2-yl)-3-cyclopentyl-1-methyl-1H-indole-6-carboxylic acid II (see Step 4) (33.36 g, 90.0 wt %, containing ~0.2 equiv of NMP from previous step, 75.00 mmol) in THF (133.4 g) was added thionyl chloride (10.71 g). The mixture was stirred at 25±5° C. for at least 1 h. After the conversion was completed as g), toluene (214 g) and N-methylpyrrolidone (1.37 g). The mixture was heated to 40° C., then added a solution of thionyl chloride (13 g) in toluene (17 g). The mixture was stirred at 40° C. for at least 0.5 h and cooled to 30° C. To a second reactor was charged with compound V (the bis-HCl salt toluene solvate from Step 8) (39.4 g), toluene (206 g) and N,N-diisopropylethylamine (70.8 g) at 25° C. The content of reactor 1 was transferred to reactor 2 at 30° C. and rinsed with toluene (50 g). The mixture was stirred at 30° C. for another 0.5 h, then charged with isopropanol (84 g) and water (108 g) while maintained the temperature at 25° C. After stirring for 10 min, remove the aqueous phase after phase cutting. To the organic phase was charged isopropanol (43 g), water (54 g) and stirred for 10 min. The aqueous phase was removed after phase cutting. The mixture was distilled under reduced pressure to remove ca. 250 mL of volatiles, followed by addition of methyl tert-butyl ether (MTBE, 238 g). The batch was stirred at 65° C. for over 1 hr, then cooled to 20 C over 1 hr and held for another 1 hr at the same temperature. The solid was filtered, rinsed with MTBE (95 g), and dried in vacuo at 80° C. to give (E)-butyl 3-(2-(1-(2-(5-bromopyrimidin-2-yl)-3-cyclopentyl-1-methyl-1H-indole-6-carboxamido)cyclobutyl)-1-methyl-1H-benzo[d]imidazol-6-yl)acrylate VII as a beige solid (50 g, 90% yield).

Step 10. Synthesis of (E)-3-(2-(1-(2-(5-Bromopyrimidin-2-yl)-3-cyclopentyl-1-methyl-1H-indole-6-carboxamido)cyclobutyl)-1-methyl-1H-benzo[d]imidazol-6-yl)acrylic acid (Compound (1))

mido)cyclobutyl)-1-methyl-1H-benzo[d]imidazol-6-yl)acrylate VII (489.0 g, 91.9 Wt %, 633.3 mmol) in THF (1298 g) and MeOH (387 g) was added 50% NaOH (82.7 g, 949.9 mmol), followed by rinse with water (978 g). The mixture was stirred between 65-68° C. for about 1 h for complete hydrolysis. The resulting solution was cooled to 35° C., and filtered through an in-line filter (0.5 micron), and rinsed with a premixed solution of water (978 g) and MeOH (387 g). The solution was heated to 60±4° C., and acetic acid (41.4 g, 689 mmol) was added over 1 h while the mixture was well agitated. The resulting suspension was stirred at 60±4° C. for 0.5 h. Another portion of acetic acid (41.4 g, 689 mmol) was charged in 0.5 h, and batch was stirred at 60±4° C. for addi-

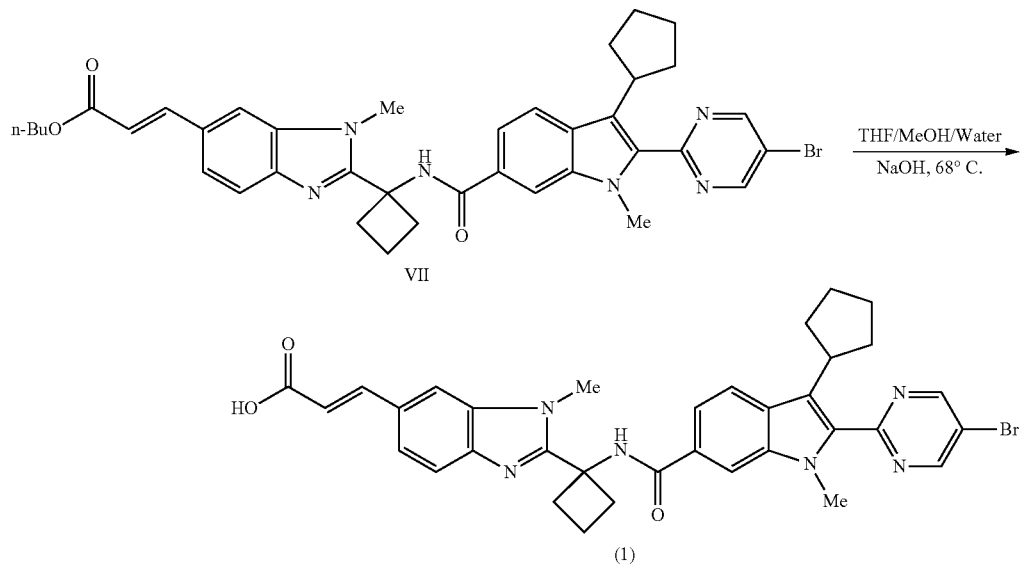

Notes:

In this process, hydrolysis of (E)-butyl 3-(2-(1-(2-(5-bromopyrimidin-2-yl)-3-cyclopentyl-1-methyl-1H-indole-6-carboxamido)cyclobutyl)-1-methyl-1H-benzo[d]imidazol-6-yl)acrylate was carried out in mixture of THF/MeOH and aq NaOH. Controlled acidification of the corresponding sodium salt with acetic acid is very critical to obtain easy-filtering crystalline product in high yield and purity.

Procedure:

To the suspension of (E)-butyl 3-(2-(1-(2-(5-bromopyrimidin-2-yl)-3-cyclopentyl-1-methyl-1H-indole-6-carboxational 0.5 h. The batch was cooled to 26±4° C. over 1 h and held for 1 h. The batch was filtered, rinsed with a premixed solution of water (1956 g) and MeOH (773.6 g), dried at 50° C. under vacuum to give (E)-3-(2-(1-(2-(5-bromopyrimidin-2-yl)-3-cyclopentyl-1-methyl-1H-indole-6-carboxamido) cyclobutyl)-1-methyl-1H-benzo[d]imidazol-6-yl)acrylic acid (1) (419.0 g, 95% yield) with ≥99.0 A % (240 nm) and 94.1 Wt % by HPLC.

Step 11. Formation of Compound (1) Sodium Salt (Type A)

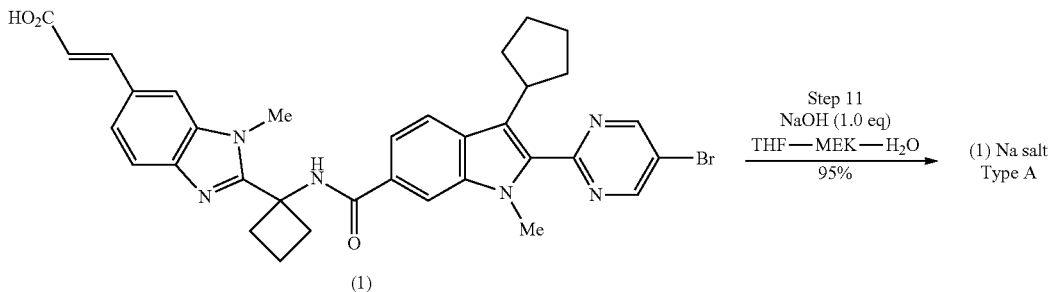

To a reactor were charged Compound (1) (150 g, 229.5 mmol), THF (492 mL), H$_2$O (51 mL) and 45% aqueous NaOH solution (20.4 g, 229.5 mmol). The mixture was stirred for >1 hr at ~25° C. to form a clear solution (pH=9-11). To the solution was charged a suspension of Charcoal (1.5 g) and H$_2$O (27 mL). The mixture was stirred at ~35° C. for >30 min and filtered. The filter was rinsed with THF (108 mL) and H$_2$O (21 mL). The filtrate was heated to 50° C. and methyl ethylketone (MEK) (300 mL) was added. The mixture was seeded with Compound (1) sodium salt MEK solvate (Type A) seeds (0.5 g) and stirred for another 1 hr at 50° C. To the mixture was charged additional MEK (600 mL). The resultant mixture was stirred for another 1 hr at 50° C. and then cooled to 25° C. The precipitate was filtered and rinsed with MEK twice (2×300 mL). The wet cake was dried in vacuum at 80° C. to give Compound (1) sodium salt (Type A) (145.6 g, 94%).

The Compound (1) sodium salt (Type A) MEK solvate seeds used in the above process step can be manufactured by the above process except without using seeds and without drying of the solvate.

Notes Regarding Crystallization Step 11

Process Optimization for Producing Higher Bulk Density Material

Observation of lab experiments showed that the seeding temperature should be reduced from 60° C. to 50° C. to prevent the dissolution of seed crystals. The crystallization kinetics in the THF/MEK/H$_2$O system was found to be slow, and oil/emulsion could be observed when anti-solvent MEK was added too fast after seeding. Thus experiments were performed to optimize the MEK addition time and aging time to minimize oiling. This improved process produced agglomerated/aggregated granular crystals consistently that resulted in the desired high bulk density.

Optimization of Anti-Solvent Addition and Aging Time

An experiment was designed to optimize the aging time following the MEK anti-solvent addition at 50° C. The data indicated that all solids crystallized out of solution within 3 hours of aging. Following aging, the slurry was cooled linearly over 2 hours to 20° C. The extended aging time did not significantly improve yield losses in the mother liquor. The crystallization resulted in a 92.4% yield.

Immediately after the completion of the MEK addition, a milky oily solution was observed along with a large amount of crystals. The oily solution dissipated within one hour. A separate experiment determined that a slower addition rate of MEK can avoid the formation of oil.

The XRPD pattern on the wet cake confirmed the MEK solvated phase.

Another experiment was carried out to adapt the process for the slow crystallization kinetics observed in the current crystallization system. A ½ hour aging time was included after seeding and the MEK anti-solvent addition time was increased from 2 to 4 hours at 50° C.

All solids were found to have crystallized out of solution within 2 hours of aging. Following aging, the slurry was cooled linearly over 2 hours to 20° C. and held overnight. This did not improve on the mother liquor losses significantly.

In conclusion, the slurry at the end of the MEK addition was found to produce clear mother liquors without an oil phase; whereas previously in the 2-hour MEK addition, a milky oily mother liquor was observed. The recommendation is for a 4-hour anti-solvent addition to prevent the oiling.

Drying Time Study

A study was conducted to determine the required drying time at 80° C. to meet the ICH limits of residual solvents of MEK and THF. The results showed that drying for a minimum of 5 hours is required to meet the ICH limit on THF.

Effects of Water Content on Yield and Crystallization

The effect of water content on crystallization was evaluated. The water content was varied from the 5.6% (w/w) level specified in the existing procedure. The study was done using 50% more and 50% less water in the crystallization. The data indicated that 5.6% water content is near optimum for good yield and operability.

Pharmaceutical Formulations of the Crystalline Sodium Salt

One class of solubilizer excipients, basifiers, act by increasing the microenvironment pH and thereby increasing the local solubility of the drug (for a drug containing an acid moiety). Another class of solubilizer excipients, surfactants, also act by increasing the local solubility of the drug. It has been found that the in vitro dissolution characteristics of Compound (1) crystalline sodium salt form can be enhanced significantly by incorporation of solubilizers, for example, surfactants, basifiers or polymers, or combinations thereof. It has also been discovered that when multiple solubilizers, such as basifiers and surfactants are used in combination with Compound (1) crystalline sodium salt, an unexpected enhancement in drug solubility is achieved, as demonstrated by in vitro testing. For example, an enhancement in dissolution was obtained when surfactants, for example, sodium lauryl sulfate or Vitamin E TPGS, were used in combination with basifiers, for example, L-arginine, meglumine or L-lysine. Powder dissolution in 500 mL pH 6.8 buffer of triturated mixtures of Compound (1) crystalline sodium salt form along with basifiers and surfactants put into capsules indicates that dissolution enhancement is observed (Table 2) when a 2:1:1 or 10:2:1 w/w triturated physical mixtures of Compound (1) sodium salt crystalline:basifier:surfactant was used compared to when 2:1 triturated physical mixtures of Compound (1) sodium salt crystalline:basifier or 2:1 triturated physical mixtures of Compound (1) sodium salt crystalline:surfactant were used. For example, only 1% drug release was obtained when Compound (1) sodium salt crystalline was present. The % drug release was 54% at 60 minutes in the presence of 100 mg Arginine alone and 59% in the presence of Sodium lauryl sulfate alone (Table 2). However, in presence of 100 mg of Arginine along with 100 mg of Sodium lauryl sulfate, the % drug release increased to 93% at 60 minutes (Table 3) indicating enhancement in dissolution when both surfactant and basifier were used in combination. Surprisingly, dissolution enhancement is also observed in the presence of only 40 mg basifier and 20 mg surfactant (for a total of 60 m g basifier+surfactant) (see Table 3) as compared to the 2:1 triturated physical mixtures having 100 mg of either basifier or surfactant.

This solubilization enhancement concept has been applied in the development of solid oral tablet formulations as described below.

TABLE 2

Dissolution of Compound (1) Na Salt in Binary Triturated Mixtures (200 mg drug & excipient(s) in capsule in 500 mL pH 6.8 buffer)

| | % Release | | | |
|---|---|---|---|---|
| | Basifiers 100 mg | | | |
| Time | Arginine (n = 4) | Meglumine (n = 2) | Lysine (n = 4) | Tris (n = 3) |
| 15 | 43 (27-53)* | 47 | 18 (9-27) | 40 (34-43) |
| 30 | 54 (39-62) | 48 | — | — |
| 60 | 54 (38-60) | 48 | 47 (33-54) | 44 (35-48) |
| 90 (infinity) | 54 (40-58) | 49 | 44 (33-46) | 41 (33-46) |

TABLE 2-continued

Dissolution of Compound (1) Na Salt in Binary Triturated Mixtures
(200 mg drug & excipient(s) in capsule in 500 mL pH 6.8 buffer)

| | Surfactant 100 mg | | | |
|---|---|---|---|---|
| | SDS (n = 2) | Vit E TPGS (n = 2) | Pluronic acid (n = 1) | Drug alone (n = 2) |
| 15 | 57 (56-57) | 24 (24-24) | 3 | 1 (1-1) |
| 30 | 61 (60-63) | 27 (27-27) | 12 | 1 (1-1) |
| 60 | 59 (58-60) | 27 (27-27) | 12 | 1 (1-2) |
| 90 (infinity) | 49 (45-53) | 27 (27-27) | 13 | 1 (1-2) |

Note, the average is reported.
*Numbers in parenthesis indicate a range of % release

TABLE 3

Dissolution of Compound (1) Na Salt in Tertiary Triturated Mixtures
(200 mg drug & excipient(s) in capsule in 500 mL pH 6.8 buffer)

Time        % Release, Average of n = 2 (range)

| | Basifier + surfactant (100 mg + 100 mg) | | | | | |
|---|---|---|---|---|---|---|
| | Arginine + SDS | Meglumine + SDS | Lysine + SDS | Arginine + VitE TPGS | Meglumine + VitE TPGS | Lysine + VitE TPGS |
| 15 | 92 (91-93) | 81 (79-83) | 40 (37-42) | 76 (74-78) | 81 (81-81) | 42 (29-55) |
| 30 | 93 (93-94) | 87 (86-88) | 74 (67-82) | 77 (76-78) | 85 (84-86) | 79 (77-81) |
| 60 | 93 (93-93) | 83 (80-87) | 85 (85-86) | 78 (78-78) | 86 (84-87) | 83 (82-83) |
| 90 | 91 (89-92) | 86 (85-87) | 85 (84-85) | 76 (75-76) | 82 (80-84) | 81 (81-82) |

| | Basifier + surfactant (40 mg + 20 mg) | | | | | |
|---|---|---|---|---|---|---|
| n = 2 | Arginine + SDS | Meglumine + SDS | Lysine + SDS | Arginine + VitE TPGS | Meglumine + VitE TPGS | Lysine + VitE TPGS − |
| 15 | 74 (70-78) | 66 (61-71) | 75 (74-77) | 62 (61-63) | 52 (33-70) | 37 (33-41) |
| 30 | 77 (74-80) | 73 (71-75) | 77 (76-78) | 64 (62-67) | 73 (73-73) | 69 (69-70) |
| 60 | 76 (74-78) | 70 (69-71) | 75 (74-75) | 65 (63-68) | 73 (73-74) | 71 (70-72) |
| 90 | 72 (70-74) | 68 (67-69) | 72 (70-74) | 63 (60-66) | 71 (70-72) | 69 69-69) |

Based upon the physicochemical characteristics of the drug substance and the solubility enhancement obtained when using surfactant and basifier in combination, the scope for the drug product development was to formulate a solid dosage formulation which would take advantage of the solubility enhancement achieved using basifiers and surfactants in combination and dissolve rapidly upon contact with aqueous media. This formulation comprises one or more basifier and one or more surfactant, which in combination can enhance the solubilization of the drug as well as maintain the drug substance in a dissolved state upon dilution in simulated intestinal fluids. Other tablet formulation components such as binders (which can also enhance solubilization), fillers, glidant and lubricants, to aid in the tabletting process, and disintegrants, to aid in tablet disintegration upon contact in aqueous media, may be added as required.

Thus, another embodiment of the present invention is directed to a solid pharmaceutical composition, e.g. a tablet, comprising:
(a) Compound (1) crystalline sodium salt;
(b) at least one surfactant;
(c) at least one basifier;
(d) and optionally one or more pharmaceutically acceptable excipients, such as binders; fillers; glidants; and lubricants.

The amount of active ingredient of Compound (1) crystalline sodium salt that may be present in the dosage form may vary widely or be adjusted depending upon the intended route of administration, the potency of the particular active ingredient being used, the severity of the hepatitis C viral infection and the required concentration. In a particular embodiment, the Compound (1) crystalline sodium salt is present in a tablet-based formulation composition in an amount from about 1% to 90% by weight, preferably from about 5% to 50% by weight, more preferably from about 10% to 40% by weight.

Pharmaceutically acceptable surfactants suitable for use in context of the present invention include, but are not limited to, sodium lauryl sulfate (SDS), Vitamin E TPGS, Gelucire® or combinations thereof. A preferred surfactant is sodium lauryl sulfate. The surfactant comprises 0% to 50% by weight of the total composition, with preferred amounts from 1-10% by weight of total composition and still more preferably from about 2% to 8% by weight of total composition.

Pharmaceutically acceptable basifiers suitable for use in context of the present invention include, but are not limited to, L-arginine, meglumine, L-lysine, tromethamine (Tris) or combinations thereof. A preferred basifier is L-arginine. The basifier comprises 0% to 40% by weight of the total composition, with preferred amounts from 2-20% by weight of total composition and more still preferably from about 4% to 16% by weight of total composition.

The composition in accordance with the invention optionally includes further excipients, such as tablet binders (e.g. water miscible polymers such as polyethylene glycols (different molecular weights) and polyvinyl pyrrolidone and water insoluble polymers such as copolymers of polyvinyl pyrrolidone and polyvinyl acetate, etc.), tablet fillers (such as microcrystalline cellulose, pharmaceutically acceptable sugars (such as lactose monohydrate, mannitol, isomalt, sorbitol, etc), glidants (such as talc, colloidal silicon dioxide, etc.), lubricants (such as magnesium stearate, etc). In this composition, the tablet binders such as polyethylene glycols (different molecular weights) also act as a solubilizer in the formulation and the composition preferable may contain such binder/solubilizer. Those of ordinary skill in the pharmaceutical art will know how to select acceptable binders, fillers, glidants and lubricants for tablet formulation.

Additionally, if in tablet form the tablet may be film coated to form as a film coated tablet product using commonly known and commercially available film coating materials. Examples of film-forming polymers that can be used include polyvinyl acetate and hydroxypropyl methyl cellulose. These polymers are present in commercially available film coating systems such as OPADRY® I and OPADRY® II systems from Colorcon.

Additional preferred formulation embodiments include:

A solid pharmaceutical composition, e.g. a tablet, comprising:
(a) about 5 to 60% by weight Compound (1) crystalline sodium salt;
(b) about 1 to 10% by weight surfactant;
(c) about 2 to 20% by weight basifier;
(d) 0 to about 40% by weight binder;
and optionally one or more pharmaceutically acceptable excipients A solid pharmaceutical composition, e.g. a tablet, comprising:
(a) about 10 to 50% by weight Compound (1) crystalline sodium salt;
(b) about 2 to 8% by weight surfactant;
(c) about 4 to 16% by weight basifier;
(d) about 1 to 25% by weight binder;
and optionally one or more pharmaceutically acceptable excipients.

A solid pharmaceutical composition, e.g. a tablet, comprising:
(a) about 20 to 50% by weight Compound (1) crystalline sodium salt;
(b) about 2 to 6% by weight surfactant;
(c) about 4 to 12% by weight basifier;
(d) about 5 to 20% by weight binder;
and optionally one or more pharmaceutically acceptable excipients.

Examples of pharmaceutical formulations containing Compound (1) include the tablet formulations described below.

Example 2

Solid Oral Formulation #1

The composition of the solid oral formulation:

| | Monograph | Functionality | % w/w |
|---|---|---|---|
| Compound (1) Na salt | | Active | 34.45 |
| Meglumine | USP/Ph. Eur. | Basifier | 7.00 |
| Sodium Lauryl Sulfate | NF/Ph. Eur. | Surfactant | 3.50 |
| Polyethylene Glycol 6000 | NF/Ph. Eur. | Solubilizer/Binder | 10.33 |
| Mannitol | USP/Ph. Eur. | Filler | 43.72 |
| Colloidal Silicon Dioxide | NF/Ph. Eur. | Glidant | 0.75 |
| Magnesium Stearate | NF/Ph. Eur. | Lubricant | 0.75 |

Two specific solid oral drug product formulations were prepared according to the above general Formulation #1, a 50 mg product and a 200 mg product.

| Ingredient | Function | 200 mg mg/tablet | 50 mg mg/tablet |
|---|---|---|---|
| Compound (1) Na salt[1] | Drug Substance | 206.7[1] | 51.7[1] |
| Meglumine | Basifier | 42.0 | 10.5 |
| Sodium Lauryl Sulfate | Surfactant | 21.0 | 5.3 |
| Polyethylene Glycol 6000 | Solubilizer Binder | 62.0 | 15.5 |
| Mannitol (powdered) | Filler | 262.3 | 65.6 |
| Purified Water[2] | Granulating agent | q.s. | q.s. |
| Colloidal Silicon Dioxide | Glidant | 3.0 | 0.8 |
| Magnesium Stearate[3] | Lubricant | 3.0 | 0.8 |
| Total | | 600.0 | 150.0 |

[1]206.7 mg and 51.7 mg Compound (1) Na salt (sodium salt) is equivalent to 200 mg and 50 mg of the active moiety, Compound (1) (free acid), respectively.
[2]Purified water is used as a granulating agent; it does not appear in the final product.
[3]Vegetable origin

Example 3

Solid Oral Formulation #2

The composition of the solid oral formulation:

| | Monograph | Functionality | % w/w |
|---|---|---|---|
| Compound (1) Na salt | | Active | 40.00 |
| Arginine | USP/Ph. Eur. | Basifier | 8.00 |
| Sodium Lauryl Sulfate | NF/Ph. Eur. | Surfactant | 4.00 |
| Polyethylene Glycol 8000 | NF/Ph. Eur. | Solubilizer/Binder | 12.00 |
| Mannitol | USP/Ph. Eur. | Filler | 35.00 |
| Colloidal Silicon Dioxide | NF/Ph. Eur. | Glidant | 0.50 |
| Magnesium Stearate | NF/Ph. Eur. | Lubricant | 0.50 |

Two specific solid oral drug product formulations were prepared according to the above general Formulation #2, a 200 mg product and a 400 mg product.

| Ingredient | Function | 200 mg mg/tablet | 400 mg mg/tablet |
|---|---|---|---|
| Compound (1) Na salt[1] | Drug Substance | 206.7[1] | 413.4[1] |
| Arginine | Basifier | 41.4 | 82.7 |
| Sodium Lauryl Sulfate | Surfactant | 20.7 | 41.3 |
| Polyethylene Glycol 8000 | Solubilizer/Binder | 62.0 | 124.0 |
| Mannitol (powdered) | Filler | 180.9 | 361.8 |
| Purified Water[2] | Granulating agent | q.s. | q.s. |
| Colloidal Silicon Dioxide | Glidant | 2.6 | 5.2 |
| Magnesium Stearate[3] | Lubricant | 2.6 | 5.2 |
| Total | | 516.8 | 1033.6 |

[1]206.7 mg and 413.4 mg Compound (1) Na salt (sodium salt) is equivalent to 200 mg and 400 mg of the active moiety, Compound (1) (free acid), respectively.
[2]Purified water is used as a granulating agent; it does not appear in the final product.
[3]Vegetable origin

Example 4

Solid Oral Formulation #3

The composition of the solid oral formulation:

| | Monograph | Functionality | % w/w |
|---|---|---|---|
| Compound (1) Na salt | | Active | 40.00 |
| Arginine | USP/Ph. Eur. | Basifier | 8.00 |
| Sodium Lauryl Sulfate | NF/Ph. Eur. | Surfactant | 4.00 |
| Polyethylene Glycol 8000 | NF/Ph. Eur. | Solubilizer/Binder | 12.00 |

-continued

| | Monograph | Functionality | % w/w |
|---|---|---|---|
| Mannitol | USP/Ph. Eur. | Filler | 15.00 |
| Isomalt | NF/Ph. Eur. | Filler | 20.00 |
| Colloidal Silicon Dioxide | NF/Ph. Eur. | Glidant | 0.50 |
| Magnesium Stearate | NF/Ph. Eur. | Lubricant | 0.50 |

Three specific solid oral drug product formulations were prepared according to the above general Formulation #3, a 200 mg product, a 300 mg product and a 400 mg product.

| Ingredient | Function | 200 mg mg/tablet | 300 mg mg/tablet | 400 mg mg/tablet |
|---|---|---|---|---|
| Compound (1) Na salt[1] | Drug Substance | 206.7[1] | 310.1 | 413.4[1] |
| Arginine | Basifier | 41.4 | 62.1 | 82.7 |
| Sodium Lauryl Sulfate | Surfactant | 20.7 | 31.1 | 41.3 |
| Polyethylene Glycol 8000 | Solubilizer/Binder | 62.0 | 93.0 | 124.0 |
| Mannitol (powdered) | Filler | 77.6 | 116.3 | 155.1 |
| Purified Water[2] | Granulating agent | q.s. | q.s. | q.s. |
| Isomalt | Filler | 103.4 | 155.0 | 206.7 |
| Colloidal Silicon Dioxide | Glidant | 2.6 | 3.9 | 5.2 |
| Magnesium Stearate[3] | Lubricant | 2.6 | 3.9 | 5.2 |
| Total | | 516.8 | 775.2 | 1033.6 |

[1]206.7 mg, 310.1 mg and 413.4 mg Compound (1) NA (sodium salt) are equivalent to 200 mg, 300 mg and 400 mg of the active moiety, Compound (1) (free acid), respectively.
[2]Purified water is used as a granulating agent; it does not appear in the final product.
[3]Vegetable origin Preparation of Formulations 1-3

The drug substance along with the intragranular excipients including the basifier, surfactant, solubilizer/binder, filler are mixed in a dry state in a high shear granulator prior to addition of water. The drug substance and the excipients may be screened prior to milling to remove large agglomerates if necessary. After mixing is complete, the mixture is granulated using purified water as a granulating agent in the high shear granulator till a suitable end point is achieved. The wet granules are removed and dried at appropriate drying temperatures either in a tray dryer or a fluid bed dryer. The dried granules are milled by passing through a high speed mill, such as a Comill. Milled granules are then blended with the extragranular excipients, including filler (for Formulation 3), glidant and lubricant and then tableted in a tablet press.

Example 5

Solid Oral Formulations #4 and #5 (Fluid Bed Granulation)

Additional formulations have been prepared using a fluid bed granulation process instead of high shear granulation. Though the formulations are very similar to those prepared using high shear granulation, this fluid bed granulation process significantly reduces the manufacturing time and enables much easier and less challenging process scale-up compared to high shear granulation. These formulations also exhibit an advantage of significantly improved tableting properties (achieving target tablet hardness at significantly reduced compression forces during tableting operation) compared to the formulations manufactured using high shear granulation.

The composition of the solid oral formulations #4 and #5 are as set forth in the table below:

| | | | Formulation # | |
|---|---|---|---|---|
| | Monograph | Functionality | #4 % w/w | #5 % w/w |
| Compound (1) Na salt | | Active | 40.00 | 40.00 |
| Arginine | USP/Ph. Eur. | Basifier | 8.00 | 8.00 |
| Sodium Lauryl Sulfate | NF/Ph. Eur. | Surfactant | 4.00 | 4.00 |
| Polyethylene Glycol 8000 | NF/Ph. Eur. | Solubilizer/Binder | 12.00 | 12.00 |
| Mannitol | USP/Ph. Eur. | Filler | 15.00 | 34.50 |
| Isomalt | NF/Ph. Eur. | Filler | 19.50 | — |
| Colloidal Silicon Dioxide | NF/Ph. Eur. | Glidant | 0.50 | 0.50 |
| Magnesium Stearate | NF/Ph. Eur. | Lubricant | 1.00 | 1.00 |

Three specific solid oral drug product formulations were prepared according to each of the above general Formulations #4 and #5, a 200 mg product, a 300 mg product and a 400 mg product.

| | | Formulation # | | | | | |
|---|---|---|---|---|---|---|---|
| | | Formulation #4 | | | Formulation #5 | | |
| Ingredient | Function | 200 mg mg/tablet | 300 mg mg/tablet | 400 mg mg/tablet | 200 mg mg/tablet | 300 mg mg/tablet | 400 mg mg/tablet |
| Compound (1) Na salt[1] | Drug Substance | 206.7[1] | 310.1[1] | 413.4[1] | 206.7[1] | 310.1[1] | 413.4[1] |
| Arginine | Basifier | 41.4 | 62.1 | 82.7 | 41.4 | 62.1 | 82.7 |
| Sodium Lauryl Sulfate | Surfactant | 20.7 | 31.1 | 41.3 | 20.7 | 31.1 | 41.3 |
| Polyethylene Glycol 8000 | Solubilizer/Binder | 62.0 | 93.0 | 124.0 | 62.0 | 93.0 | 124.0 |
| Mannitol (powdered) | Filler | 77.5 | 116.3 | 155.0 | 178.3 | 267.4 | 356.6 |
| Purified Water[2] | Granulating agent | q.s. | q.s. | q.s. | q.s. | q.s. | q.s. |
| Isomalt | Filler | 100.8 | 151.2 | 201.6 | — | — | — |
| Colloidal Silicon Dioxide | Glidant | 2.6 | 3.9 | 5.2 | 2.6 | 3.9 | 5.2 |
| Magnesium | Lubricant | 5.2 | 7.8 | 10.3 | 5.2 | 7.8 | 10.3 |

-continued

| | | Formulation # | | | | | |
|---|---|---|---|---|---|---|---|
| | | Formulation #4 | | | Formulation #5 | | |
| Ingredient | Function | 200 mg mg/tablet | 300 mg mg/tablet | 400 mg mg/tablet | 200 mg mg/tablet | 300 mg mg/tablet | 400 mg mg/tablet |
| Stearate[3] | | | | | | | |
| Total | | 516.8 | 775.2 | 1033.6 | 516.8 | 775.2 | 1033.6 |

[1] 206.7 mg, 310.1 mg and 413.4 mg Compound (1) NA (sodium salt) are equivalent to 200 mg, 300 mg and 400 mg of the active moiety, Compound (2) (free acid), respectively.
[2] Purified water is used as a granulating agent; it does not appear in the final product.
[3] Vegetable origin Preparation of Formulations 4 and 5 Via Fluid Bed Granulation The general procedure for preparation of both Formulations #4 and #5 is the same. An aqueous binder solution containing PEG 8000 (binder/solubilizer) or containing both PEG 8000 (binder/solubilizer) and arginine (basifier) is prepared first. The other intragranular components, including active ingredient, surfactant, filler and basifier (optional, depending upon composition of the binder solution) are mixed in the dry state for ~5 minutes in the fluid bed granulator to prepare the premixture. The premixture is maintained in a fluidized state and granulated by spraying the binder solution first followed by water into the fluid bed granulator, while adjusting process parameters such as product bed temperature, inlet air temperature, airflow rate, spray rate and atomization pressure as required. Drying of the granulation is continued by maintaining the granulation in a fluidized state at an elevated temperature until a desired end point of drying (loss on drying) is obtained. The dried granules are milled by passing through a high speed mill, such as a Comill Milled granules are then blended with the extragranular excipients, including filler, glidant and lubricant and then tableted in a tablet press. The core tablets obtained are further film coated using a standard film coating formulation, such as, Hydroxypropylmethyl cellulose-based standard OPADRY® or Polyvinylacohol-based OPADRY® II.

The Amorphous Sodium Salt Form

The dissolution characteristics of the drug can be further improved significantly by conversion of the crystalline sodium salt form to the amorphous sodium salt form. Powder dissolution testing in pH 6.8 buffer using a USP Type II Paddle apparatus and comparing Compound (1) sodium salt amorphous form prepared via solvent evaporation technique to Compound (1) sodium salt crystalline form clearly shows significant improvement in kinetic dissolution with the amorphous Compound (1) sodium salt dissolving about 35% at 60 minutes compared to the crystalline Compound (1) sodium salt which dissolves <5%.

The glass transition temperature of the amorphous form of Compound (1) sodium salt is >200° C., which is quite atypical for pharmaceutical active materials and can be considered an unexpected finding. Due to the fact that this amorphous material exhibits an unusually high glass transition temperature, the amorphous form of Compound (1) sodium salt exhibits acceptable physical and chemical stability under accelerated storage conditions, which makes it a very promising candidate for amorphous drug product development.

Typical procedures for manufacturing the amorphous form of Compound (1) sodium salt include, but are not limited to, processing Compound (1) sodium salt by itself or coprocessing it with common pharmaceutical quality excipients, such as hydrophilic polymers, for example, polyvinyl pyrrolidone of different molecular weights, copolymers of polyvinyl pyrrolidone and polyvinyl acetate, polyethylene glycol, hydroxypropylmethyl cellulose, etc to obtain solid dispersions. Common techniques for producing the amorphous form of Compound (1) sodium salt include, but are not limited to milling, solvent evaporation, hot melt extrusion, etc.

Pharmaceutical Formulation of the Amorphous Sodium Salt Form

One technique that has been extensively investigated for formulating amorphous Compound (1) sodium salt is the use of Hot Melt Extrusion (HME) processing to prepare amorphous Solid Dispersions (SD) formulations. A modified HME processing technique involving the use of a volatile solvent to act as both a transient plasticizer and transient solubilizer has been implemented to efficiently prepare amorphous solid dispersions of high drug loading. It is believed that the unique and unexpected solubilizing behavior of Compound (1) sodium salt, as hereinbefore described, makes such modified HME processing using a volatile solvent a viable technique for preparing high-drug loading amorphous solid dispersions.

1. Background

Solid dispersions (SDs) have been used as an effective method to improve dissolution properties and bioavailability of poorly water soluble drugs. The melting technique is one of the most widely used methods to prepare amorphous solid dispersions. Hot melt extrusion (HME) technique, which represents a novel application of polymer processing technology to prepare pharmaceutical dosage forms, has in recent years been increasingly used to prepare SDs of poorly soluble drug. HME is a process of pumping raw materials with a rotating screw under elevated temperature through a die into a product of uniform shape.

The challenge to overcome processing a therapeutic compound using a hot melt extrusion method is to effectively plasticize the polymeric carrier. Processing temperature above the Tg or melting temperature of the polymeric carrier is typically required to soften and lower the polymer melt viscosity to allow adequate flow through the extruder. The addition of a plasticizer will decrease the polymer Tg due to intermolecular interaction with the polymeric chains allowing for lower processing temperatures. Lowering the polymer Tg with plasticizers, therefore, facilitates thermal stability of the composite materials. Various polymers and saccharides are generally used as carriers for SDs. In the case of using a water soluble polymer as a carrier for SDs, it is expected that lowering the glass transition temperature (Tg) of the polymer would allow for the preparation of amorphous SDs by heating below the melting temperature of the drug. Therefore, using a plasticizer to act with the polymer is thought to be effective to decrease drug degradation in the SDs. Traditional plasticizers used in HME such as TEC, PEG, triacetin, glycerin, diethyl phthalate, propylene glycol are associated with such limitations as toxicity and moderate water solubility. Alternatively surfactant based plasticization serves the dual purpose of aiding polymer processing, as well as subsequent API solubilization and bioavailability enhancement. However adding a plasticizer lowers the Tg of SDs, and this can thus easily induce drug crystallization. It is also possible for the surfactant to destabilize the system by lowering the Tg and increasing the water uptake.

Another challenge for preparing a solid dispersion system by HME is when the therapeutic compounds are used at high doses, because higher drug loading in the system is needed to ensure acceptable unit size for oral administration. The amount of the polymer carrier in the SD is often limited especially additional solubilizing agents such as surfactants and basic or acidic agents are needed to further improve solubility. In such cases, plasticizing the polymer alone will not be sufficient to reduce the viscosity of the extruding mixture due to limited quantity of the polymer present in the system.

Some HME-related techniques that have been used include:
1. Lowering Tg of the polymer during HME by adding plasticizers such as TEC, PEG, triacetin, glycerin, diethyl phthalate, propylene glycol have been reported in the literature.
2. Use some of the surfactants as plasticizers has also been reported to serves the dual purpose of aiding polymer processing, as well as subsequent API solubilization and bioavailability enhancement.
3. Preparation of a solid dispersion with 0% crystallinity by controlling heating temperature and water content in a drug-polymer physical mixture in a sealed glass ampoule has been reported in the literature.
4. A liquefied gas, such as supercritical CO2, has been claimed to serve as a transient plasticizer to facilitate the processing of the materials during extrusion (see US Application 2008/0280999).

Disadvantages of the some of the known HME-related plasticization techniques include:
1. Adding a non-volatile plasticizer lowers the Tg of solid dispersions permanently, and this can thus easily induce drug crystallization. In addition, the mechanical, thermal and gas and moisture permeation properties of the solid dispersions could also be changed.
2. Adding surfactant as a plasticizer is likely to destabilize the system by lowering the Tg and increasing the water uptake as reported in the literature.
3. Traditional plasticizers used in HME such as TEC, PEG, triacetin, glycerin, diethyl phthalate, propylene glycol are associated with such limitations as toxicity and moderate water solubility.

2. Modified HME Process

The modified HME process technique of the present invention involves the use of a volatile solvent such as water, ethanol or other volatile solvents during the HME process. The volatile solvent serves two purposes: (1) to plasticize the polymer carrier by lowering the Tg of the polymer, (2) to practically solubilize the compound and excipients present in the extruding mixture. The combination of (1) and (2) above can lead to sufficient reduction of the viscosity of the extruding materials, allowing extrusion to be conducted at a lower temperature that is below the melting point of the compound. Since the volatile solvent is evaporated out after the extrusion process, the final extruded SD will maintain the high Tg which is necessary to ensure physical and chemical stability of the SD system. The requirement for the therapeutic compounds is that they should have reasonable solubility ($>=1$ mg/mL) in the volatile solvents. These include but not limited to those poorly soluble compounds, such as Compound (1) sodium salt, that can self-micellize to form micelle at high concentration in aqueous or other volatile solvents.

3. Embodiments

In general, the modified HME process of the present invention can be summarized as follows:

Equilibrate the extruder along with proper screw configuration to desired extruding temperature. Using a mechanical mixer blend all the formulation components together to be extruded using a hot melt extrusion process. Mix the blended powder with water to form a wet mass which can then be fed into the equilibrated extruder for hot melt extrusion. In addition, volatile solvents such as ethanol, isopropanol or water, alone or in any combination thereof, can be used for the preparation of the wet mass. The extrudates are then dried in a convection oven at 60° C. for a period of time. Dried extrudates are screened through a 20-mesh (850 µm) screen. The screened extrudates can be used as is or can be blended with dry excipients such as mannitol, colloidal silicon dioxide and magnesium stearate. The blended material can be filled in to a capsule or compressed into a tablet.

Alternatively, for the hot melt extrusion process, the blended powder can be passed into the equilibrated extruder barrel along with simultaneously injecting liquid water to form the wet mass for the hot melt extrusion process. The injected liquid can be a volatile solvent such as water, ethanol, isopropanol, either alone or combined in any proportions. These volatile solvents or blends thereof can act as transient plasticizers as well as solubilizers to dissolve the drug as well as the other soluble components.

In view of the general applicability of this modified HME process, one general embodiment of the invention can be defined as a process for preparing an amorphous formulation comprising the following steps (1) to (4) or (5) to (8):
(1) mixing an active pharmaceutical ingredient, a polymer, a volatile solvent and, optionally, a soluble excipient to form a wet mass;
(2) feeding the wet mass into a temperature equilibrated extruder to form an extrudate;
(3) drying the extrudate;
(4) optionally screening the dried extrudates and mixing them with additional pharmaceutically acceptable excipients;
or:
(5) mixing an active pharmaceutical ingredient, a polymer and, optionally, a soluble excipient to form a mixture;
(6) feeding the mixture and a volatile solvent simultaneously into a temperature equilibrated extruder to form an extrudate;
(7) drying the extrudate;

(8) optionally screening the dried extrudates and mixing them with additional pharmaceutically acceptable excipients;

As mentioned above, the active pharmaceutical ingredient (API) should be one having reasonable solubility (>=1 mg/mL) in the volatile solvent selected.

The amount of transient plasticizer or volatile components, or the blend thereof, can range from 2% to 70% in the hot melt extrusion process.

Examples of solvents, polymers and other soluble excipients that may be used in the process include, for example:

1. Volatile solvents with both plasticizing and solubilizing capabilities: e.g., water and other volatile solvents such as ethanol, isoproponal, may be suitable as a plasticizer for some polymers or polymer blends who's Tg could be greatly reduced with increasing amount of such plasticizer and may further act as a solubilizer to practically dissolve the compound or other water soluble excipients in the system.

2. Polymers: polyvinylpyrolidone (PVP), polyethylene glycol (different molecular weights), copolymers of polyvinyl pyrrolidone and polyvinyl acetate, Eudragit type polymers, polyethylene oxide, hydroxypropyl methyl cellulose and other amorphous polymers or polymer blends who's Tg can be greatly reduced by volatile plasticizers will be suitable for this application. Many hydrophilic, ionic, H-bonding polymers including both synthetic and natural ones are included in this category.

3. Soluble excipients: functional excipients such as basifying (L-arginine, meglumine, L-lysine or tromethamine or combinations thereof, inorganic basifiers or combinations thereof) or acidifying agents, surfactants (sodium lauryl sulfate (SDS), Vitamin E TPGS, Gelucire or sodium docusate or combinations thereof), polymers such as PEG 8000 that can be dissolved or practically dissolve in water or other volatile solvents are suitable for use to reduce the viscosity of the extruding mixture.

After drying and screening, the extrudates may be further mixed with additional pharmaceutically acceptable excipients such as tablet binders, tablet fillers (such as microcrystalline cellulose, pharmaceutically acceptable sugars (such as lactose monohydrate, mannitol, isomalt, sorbitol, etc), glidants (such as talc, colloidal silicon dioxide, etc.) and lubricants (such as magnesium stearate, etc), prior to tabletting. Those of ordinary skill in the pharmaceutical art will know how to select acceptable binders, fillers, glidants and lubricants for tablet formulation. Coatings may also be applied as needed.

Another general embodiment is directed to a pharmaceutical composition comprising Compound (1) sodium salt in amorphous form and at least one pharmaceutically acceptable carrier or diluent.

In a more specific embodiment, the final pharmaceutical composition that may be prepared by the HME process as herein described is a solid pharmaceutical composition, e.g. a tablet, comprising:
(a) amorphous Compound (1) sodium salt;
(b) at least one surfactant;
(c) at least one basifier;
(d) at least one polymer;
(e) and optionally one or more pharmaceutically acceptable excipients.

Additional sub-embodiments include the following compositions:

A solid pharmaceutical composition, e.g. a tablet, comprising:
(a) 1% to 90% by weight amorphous Compound (1) sodium salt;
(b) 1% to 50% by weight surfactant;
(c) 1% to 50% by weight basifier;
(d) 1% to 99% by weight polymer;
(e) and optionally one or more pharmaceutically acceptable excipients.

A solid pharmaceutical composition, e.g. a tablet, comprising:
(a) 1% to 80% by weight amorphous Compound (1) sodium salt;
(b) 1% to 30% by weight surfactant;
(c) 2% to 40% by weight basifier;
(d) 10% to 80% by weight polymer;
(e) and optionally one or more pharmaceutically acceptable excipients.

A solid pharmaceutical composition, e.g. a tablet, comprising:
(a) 1% to 70% by weight amorphous Compound (1) sodium salt;
(b) 2% to 20% by weight surfactant;
(c) 5% to 20% by weight basifier;
(d) 20% to 70% by weight polymer;
(e) and optionally one or more pharmaceutically acceptable excipients.

A solid pharmaceutical composition, e.g. a tablet, comprising:
(a) 30% to 60% by weight amorphous Compound (1) sodium salt;
(b) 2% to 10% by weight surfactant;
(c) 5% to 15% by weight basifier;
(d) 20% to 40% by weight polymer;
(e) and optionally one or more pharmaceutically acceptable excipients.

In additional sub-embodiments, the surfactant is SDS (sodium dodecyl sulfate), the basifier is Arginine and the polymer is PVP K25.

One exemplary formulation is set forth below:

| Component | % (W/W) |
| --- | --- |
| Compound (1) Na salt | 50.63 |
| SDS (Surfactant) | 5.06 |
| Arginine (Basifier) | 10.13 |
| PVP K25 (Polymer) | 34.18 |
| Total | 100 |

4. Characterization of HME Granules Prepared Using Water as Transient Plasticizer/Solubilizer I. Composition of the Solid Dispersion Formulation The SD formulation used for extrusion experiments is shown in Table 4:

TABLE 4

Composition of Compound (1) Na salt solid dispersion (Blend #1)

| Component | % (W/W) |
| --- | --- |
| Compound (1) Na salt | 50.63 |
| SDS (sodium dodecyl sulfate) | 5.06 |
| Arginine | 10.13 |
| PVP K25 | 34.18 |
| Total | 100 |

II. Preparation of Solid Dispersion of Blend #1 Using Twin Screw Extruder

PVP K25 is used as the polymer carrier because it increases the solubility of Compound (1) Na salt in aqueous media. PVP K25 has a glass transition temperature of ~150° C. With a high drug load (50.63%) in the mixture blend of Table 4 and the high melt/decomposition temperature of the drug (~320° C.), extruding this mixture blend without adding plasticizer did not work (jamming occurred on a bench-top twin screw extruder), even when the barrel temperature was heated up to 200° C. Small trial extrusion runs were carried out at 5-10 g scale using a 9 mm bench-top twin screw extruder. Various amount of water was added to the Blend #1 prior to the extrusion. It was found that extrudates could be successfully produced at temperature below 100° C. with the water content between 20-35% (w/w) in the powder blend.

A larger scale extrusion run was then performed using a Leistritz 16 mm extruder at 100-300 g scale. The Blend #1 was mixed with water (water content 31% w/w in the mixture). The mixture was loaded into a forced feeder with is attached vertically to the Leistritz 16 mm extruder. The temperature of the barrels was set at 90° C. for Zone 1-4. The extruder speed was set at 60 rpm. It should be noted that the water content in the blend mixture when it flows through the extruder may be less than 31% due to some water evaporation under the high barrel temperature (90° C.). Transparent extrudate was produced through the 2 mm die plate. The motor load was ~25%, indicating a low internal barrel pressure. The extrudate was non-sticky, dried quickly at room temperature.

The extrudates were further dried in a 60° C. oven for ~8 hrs and then were milled through a 20 mesh (850 um) screen to obtain fine granules. The granules have good flowability and can be easily filled into hard shell capsules.

Figure 10:
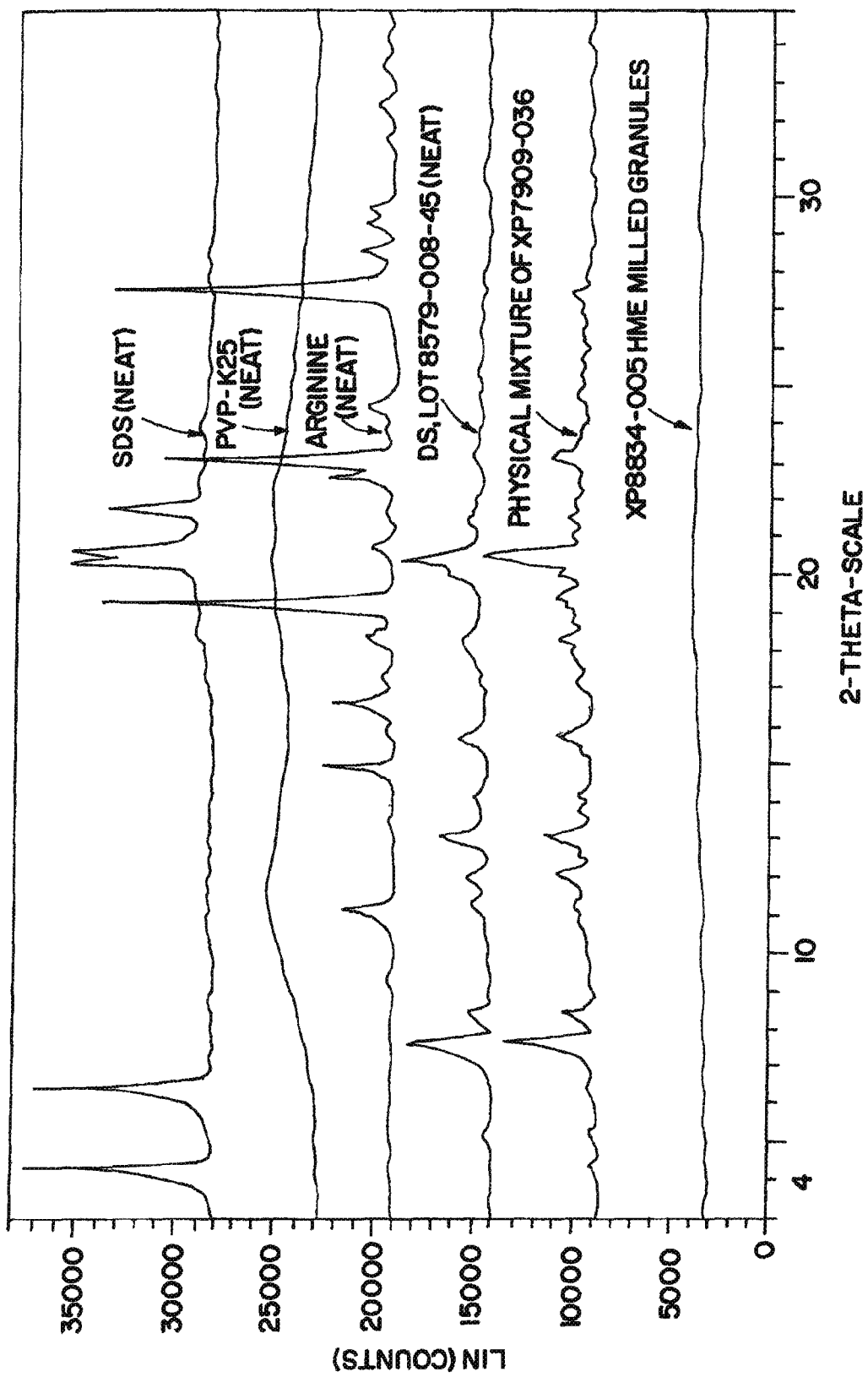
FIG. 10 shows a representative XRPD diffraction pattern of hot-melt extruded granules containing amorphous Compound (1) sodium salt, in comparison with the XRPD pattern of the individual components and the physical mixture.

III. Characterizations of the Solid Dispersion (HME Granules) Produced Using Water as a Transient Solubilizer and Plasticizer An XRPD analysis of the extruded granules in comparison with the corresponding physical mixture was performed, as well as for the individual components for comparison purposes. The XRPD pattern of the extruded granules containing amorphous Compound (1) sodium salt, in comparison with the XRPD pattern of the individual components and the physical mixture, is shown in FIG. 10 (HME granules=bottom pattern; "DS"=Compound (1) sodium salt, the third pattern from bottom). The lack of any diffraction peaks for the API (Compound (1) Na salt) in the HME granules indicates that the API has been converted to amorphous form in the solid dispersion.

To demonstrate the ability of ssNMR to identify the amorphous sodium salt of Compound (1) in a pharmaceutical dosage form, hot-melt extruded granules containing amorphous Compound (1) Na salt were analyzed by ssNMR. A mixture of Compound (1) Na salt, PVP K25 and water was prepared in a weight ratio of active/PVP-K25/water=1:1:1.33. This mixture was then subject to hot-melt extrusion using the same process as specified above (except at a barrel temperature of 110-120° C.) to obtain granules. These HME granules were then analyzed by ssNMR under the same ssNMR conditions and using the same equipment as outlined above for the NMR analysis of the crystalline API material.

Figure 11:
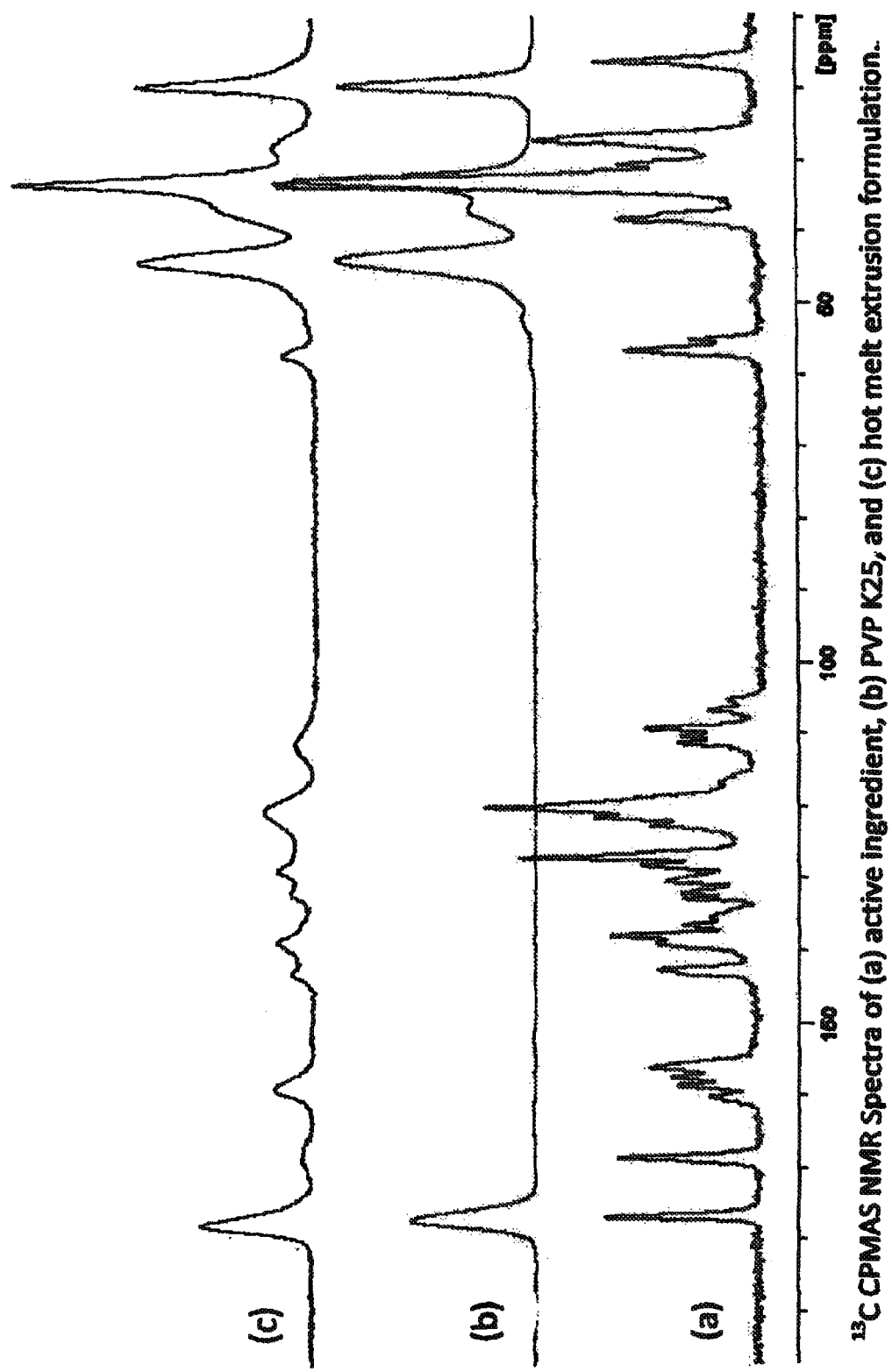
FIG. 11 shows a representative $^{13}C$ ssNMR spectrum of hot-melt extruded granules containing amorphous Compound (1) sodium salt as spectrum (c), along with a comparison ssNMR plot of the crystalline active ingredient (Type A) as spectrum (a), and a comparison ssNMR plot of PVP K25 as spectrum (b).

The $^{13}$C ssNMR spectrum of the extruded granules containing amorphous Compound (1) sodium salt, in comparison with the ssNMR spectra of the crystalline active ingredient material (Type A) and PVP K25, is shown in FIG. 11, clearly showing the peaks in the HME granules that are due to the presence of amorphous active ingredient. The NMR spectrum of the hot-melt extrusion formulation shows broadened NMR resonances for the active ingredient due to the lack of crystalline order in the amorphous form of the active ingredient. Due to significant peak broadening, spectra resolution is reduced and overlapping of closely adjacent peaks is observed for the amorphous drug in the hot-melt extrudates. Accordingly, the chemical shift range for such peaks is necessary broader than for the active ingredient and the chemical shifts reported and claimed herein for the amorphous form of the active are accurate to within ±3 ppm unless otherwise indicated.

The primary $^{13}$C chemical shifts for the amorphous Compound (1) sodium salt, as seen in the ssNMR analysis of the extruded granules, are as set forth in the following table:

| Peak (ppm ± 3 ppm) |
| --- |
| 158.4 |
| 142.9 |
| 138.3 |
| 131.5 |
| 128.3 |
| 120.2 |
| 111.0 |

One general embodiment is directed to an amorphous sodium salt of Compound (1) that has a $^{13}$C solid state NMR spectrum comprising peaks at chemical shifts of 158.4, 138.3 and 120.2 ppm (±3 ppm). These three peaks in the NMR spectrum are believed to be sufficient to uniquely identify the presence of the amorphous form of Compound (1) sodium salt.

Another general embodiment is directed to an amorphous sodium salt of Compound (1) that has a $^{13}$C solid state NMR spectrum comprising peaks at chemical shifts of 158.4, 142.9, 138.3, 131.5, 128.3, 120.2 and 111.0 ppm (±3 ppm).

All of the solid state NMR embodiments and corresponding claimed embodiments as set forth herein represent the solid state NMR of the amorphous sodium salt of Compound (1) when conducted under ambient laboratory conditions (temperature 17-25° C.; relative humidity 30-60%).

Additional embodiments are directed to pharmaceutical compositions comprising amorphous Compound (1) sodium salt wherein the amorphous Compound (1) sodium salt in the pharmaceutical composition is as defined by the above-mentioned ssNMR embodiment.

The moisture content of the milled HME granules was determined by TGA and was 4.4%. Modulated DSC was performed to assess the glass transition temperatures of the following samples.

1. HME milled granules—samples were gently triturated to break large aggregates
2. HME milled granules containing 20% water—samples were gently triturated and then mixed with water immediately before the DSC run.
3. PVP K25 polymer
4. PVP K25 polymer mixed with 20% water Samples were run in an aluminum hermetic pan without pinhole to prevent water loss during the DSC experiments. The Tg is about 172° C. for the HME granules while it is reduced to about 50° C. for the granules containing 20% water. This decrease in Tg of the solid dispersion blend due to the presence of water allows the extrusion process to be operated at below 100° C. For comparison purpose, the mDSC results for the polymer PVP K25 are also shown in the FIG. 2. The neat polymer has a Tg about 157° C. while the Tg was reduced to about 30° C. when the powder contains 20% water. These data are consistent with the literature reports where the Tg of PVP K30 is reduced to ~40° C. with 20% (w/w) water in the polymer.

In vitro dissolution testing of the SD (HME granules) and the physical mixture have demonstrated a rapid and high drug release (>90%) observed for the HME granules while only about 40% of drug was released for the physical mixture, demonstrating the advantageous dissolution behavior of the HME granules.

Another example of a specific hot melt extrusion process for preparing the amorphous form of Compound (1) sodium salt, as well as a solid oral pharmaceutical formulation containing such amorphous form, is provided below.

Example 6

Solid Oral Formulation #6

The composition of the solid dispersion oral formulation:

|  | Monograph | Functionality | % w/w |
|---|---|---|---|
| Compound (1) sodium salt[1] |  | Active | 40.00 |
| L-Arginine | USP/Ph. Eur. | Basifier | 8.00 |
| Sodium Lauryl Sulfate | NF/Ph. Eur. | Surfactant | 4.00 |
| Polyvinylpyrrolidone K-25 | NF/Ph. Eur. | Solubilizer/Binder | 27.00 |
| Mannitol | USP/Ph. Eur. | Filler | 20.00 |
| Colloidal Silicon Dioxide | NF/Ph. Eur. | Glidant | 0.50 |
| Magnesium Stearate | NF/Ph. Eur. | Lubricant | 0.50 |

[1]Crystalline form of Compound (1) sodium salt is used at the start of the process and the amorphous form of Compound (1) sodium salt is obtained at the end of the Hot Melt Extrusion Step One specific solid oral drug product formulations was prepared according to the above general Formulation #6, a 400 mg product:

| Ingredient | Function | 400 mg mg/tablet |
|---|---|---|
| Compound (1) sodium salt | Drug Substance | 413.4[1] |
| Arginine | Basifier | 82.7 |
| Sodium Lauryl Sulfate | Surfactant | 41.3 |
| Polyvinylpyrrolidone K-25 | Solubilizer/Binder | 279.1 |
| Purified Water | Transient Plasticizer | q.s. |
| Mannitol (powdered) | Filler | 206.7 |
| Colloidal Silicon Dioxide | Glidant | 5.2 |
| Magnesium Stearate | Lubricant | 5.2 |
| Total |  | 1033.6 |

Preparation of Formulation #6:

Compound (1) sodium salt along with the basifier, surfactant and solubilizer/binder are mixed in a dry state in a turbula mixer. This dry mixture is further mixed with water to form a wet mass. This wet mass is then fed into and extruded through a Hot Melt Extruder operated at a temperature of 80-100° C., which consists of two intermeshed corotating screws with a small clearance inside a barrel. The material is conveyed through the barrel due to the co-rotating action of the two screws and the crystalline form of Compound (1) sodium salt is converted into the amorphous state due to the high shear energy that the material is acted upon, inside the twin screw extruder. Water acts as transient plasticizer, aiding the extrusion process. Majority of the water is evaporated during the extrusion process. The extrudates obtained are dried in a convection oven at 40° C. to 80° C. to further remove the remaining water. Dried extrudates are screened through a suitably sized-screen using a standard dry milling equipment, such as a Comil. The milled extrudates are further blended with the filler, glidant and lubricant and compressed into a tablet of suitable hardness.

The invention claimed is:
1. A crystalline sodium salt of the compound of the following formula (1):

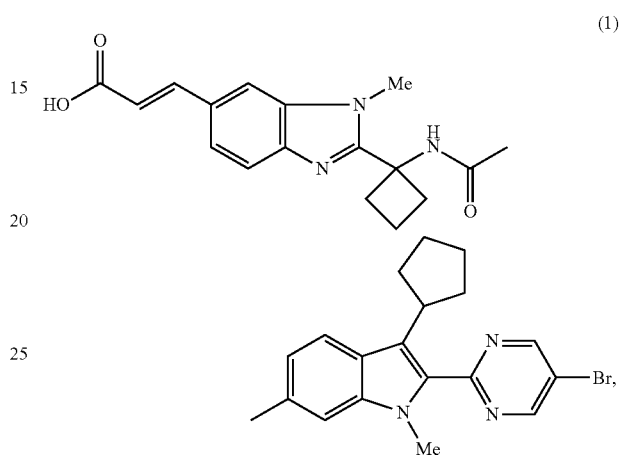

having:
(a) an X-ray powder diffraction pattern comprising peaks at 7.5 and 20.4 degrees 2θ (±0.2 degrees 2θ) when measured using CuKα radiation; or
(b) a $^{13}$C solid state NMR spectrum comprising peaks at a chemical shift of 176.8 and 168.4 ppm (±0.2 ppm); or
(c) both an X-ray powder diffraction pattern comprising peaks at 7.5 and 20.4 degrees 2θ (±0.2 degrees 2θ) when measured using CuKα radiation and a $^{13}$C solid state NMR spectrum comprising peaks at a chemical shift of 176.8 ppm and 168.4 ppm (±0.2 ppm).

2. The crystalline sodium salt according to claim 1, having an X-ray powder diffraction pattern comprising peaks at 7.5 and 20.4 degrees 2θ (±0.2 degrees 2θ) when measured using CuKα radiation.

3. The crystalline sodium salt according to claim 2, having an X-ray powder diffraction pattern comprising peaks at 7.5, 20.0 and 20.4 degrees 2θ (±0.2 degrees 2θ) when measured using CuKα radiation.

4. The crystalline sodium salt according to claim 1, having an X-ray powder diffraction pattern comprising peaks at 7.5, 13.1, 18.3, 20.0, 20.4 and 21.4 degrees 2θ (±0.2 degrees 2θ) when measured using CuKα radiation.

5. The crystalline sodium salt according to claim 1, having an X-ray powder diffraction pattern comprising peaks at 5.2, 7.5, 8.4, 13.1, 18.3, 20.0, 20.4, 21.4, 23.1 and 25.4 degrees 2θ (±0.2 degrees 2θ) when measured using CuKα radiation.

6. The crystalline sodium salt according to claim 1, having a $^{13}$C solid state NMR spectrum comprising peaks at chemical shifts of 176.8 and 168.4 ppm (±0.2 ppm).

7. The crystalline sodium salt according to claim 1, having a $^{13}$C solid state NMR spectrum comprising peaks at chemical shifts of 176.8, 168.4 and 16.0 ppm (±0.2 ppm).

8. The crystalline sodium salt according to claim 1, having a $^{13}$C solid state NMR spectrum comprising peaks at chemical shifts of 176.8, 168.4, 142.5, 137.7, 126.7, 119.9, 108.9 and 16.0 ppm (±0.2 ppm).

9. The crystalline sodium salt according to claim 1, having a $^{13}$C solid state NMR spectrum comprising peaks at chemical shifts of 176.8, 168.4, 142.5, 137.7, 126.7, 119.9, 108.9, 37.7 and 16.0 ppm (±0.2 ppm).

10. The crystalline sodium salt according to claim 1 having an X-ray powder diffraction pattern comprising peaks at 7.5 and 20.4 degrees 2θ (±0.2 degrees 2θ) when measured using CuKα radiation and a $^{13}$C solid state NMR spectrum comprising peaks at chemical shifts of 176.8 and 168.4 ppm (±0.2 ppm).

11. The crystalline sodium salt according to claim 1 having an X-ray powder diffraction pattern comprising peaks at 7.5, 20.0 and 20.4 degrees 2θ (±0.2 degrees 2θ) when measured using CuKα radiation and having a $^{13}$C solid state NMR spectrum comprising peaks at chemical shifts of 176.8, 168.4 and 16.0 ppm (±0.2 ppm).

12. The crystalline sodium salt according to claim 1 having an X-ray powder diffraction pattern comprising peaks at 7.5, 18.3, 20.0, 20.4, 21.4, 23.1 and 25.4 degrees 2θ (±0.2 degrees 2θ) when measured using CuKα radiation and having a $^{13}$C solid state NMR spectrum comprising peaks at chemical shifts of 176.8, 168.4, 142.5, 137.7, 126.7, 119.9, 108.9 and 16.0 ppm (±0.2 ppm).

13. The crystalline sodium salt according to claim 1 having an X-ray powder diffraction pattern comprising peaks at 5.2, 7.5, 8.4, 13.1, 18.3, 20.0, 20.4, 21.4, 23.1 and 25.4 degrees 2θ (±0.2 degrees 2θ) when measured using CuKα radiation and having a $^{13}$C solid state NMR spectrum comprising peaks at chemical shifts of 176.8, 168.4, 142.5, 137.7, 126.7, 119.9, 108.9, 37.7 and 16.0 ppm (±0.2 ppm).

14. The crystalline sodium salt according to claim 1 in substantially pure form.

15. A process for preparing the crystalline sodium salt according to claim 1
said process comprising the following steps:
   (a) reacting Compound (1) with an aqueous NaOH solution in a suitable solvent to form a clear solution;
   (b) adding methyl ethylketone to the mixture obtained in step (a) while heating the mixture to a temperature of about 50-60° C.;
   (c) optionally, adding Compound (1) sodium salt methyl ethylketone solvate seeds to the mixture obtained in step (b) at about 50° C.;
   (d) adding additional methyl ethylketone to the mixture obtained in step (b) or (c) at about 50° C.; and
   (e) cooling the mixture obtained in step (d) to about 25° C., resulting in precipitation of Compound (1) sodium salt crystals.

16. A pharmaceutical composition comprising a crystalline sodium salt of the compound of the following formula (1):

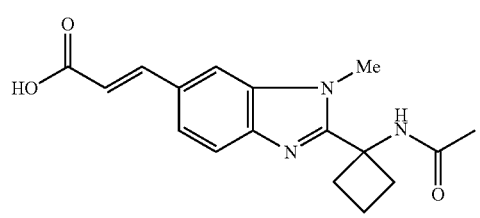

(1)

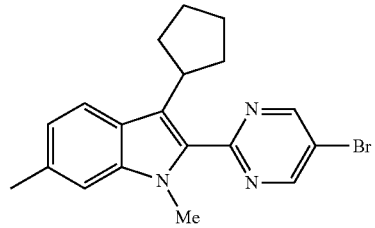

and at least one pharmaceutically acceptable carrier or diluent, wherein the crystalline sodium salt has:
   (a) an X-ray powder diffraction pattern comprising peaks at 7.5 and 20.4 degrees 2θ (±0.2 degrees 2θ) when measured using CuKα radiation; or
   (b) a $^{13}$C solid state NMR spectrum comprising peaks at chemical shifts of 176.8 and 168.4 ppm (±0.2 ppm); or
   (c) both an X-ray powder diffraction pattern comprising peaks at 7.5 and 20.4 degrees 2θ (±0.2 degrees 2θ) when measured using CuKα radiation and a $^{13}$C solid state NMR spectrum comprising peaks at chemical shifts of 176.8 ppm and 168.4 ppm (±0.2 ppm).

17. The pharmaceutical composition according to claim 16, wherein the crystalline sodium salt is in substantially pure form.

18. A pharmaceutical composition according to claim 16 comprising:
   (a) Compound (1) crystalline sodium salt;
   (b) at least one surfactant;
   (c) at least one basifier;
   and optionally one or more pharmaceutically acceptable excipients.

19. A pharmaceutical composition according to claim 16 comprising:
   (a) about 5 to 60% by weight of Compound (1) crystalline sodium salt;
   (b) about 1 to 10% by weight surfactant;
   (c) about 2 to 20% by weight basifier;
   (d) 0 to about 40% by weight binder;
   and optionally one or more pharmaceutically acceptable excipients.

20. A pharmaceutical composition according to claim 16 comprising:
   (a) about 10 to 50% by weight Compound (1) crystalline sodium salt;
   (b) about 2 to 8% by weight surfactant;
   (c) about 4 to 16% by weight basifier;
   (d) about 1 to 25% by weight binder;
   and optionally one or more pharmaceutically acceptable excipients.

21. A pharmaceutical composition according to claim 16 comprising:
   (a) about 20 to 50% by weight Compound (1) crystalline sodium salt;
   (b) about 2 to 6% by weight surfactant;
   (c) about 4 to 12% by weight basifier;
   (d) about 5 to 20% by weight binder;
   and optionally one or more pharmaceutically acceptable excipients.

22. A sodium salt of the compound of the following formula (1) in amorphous form:

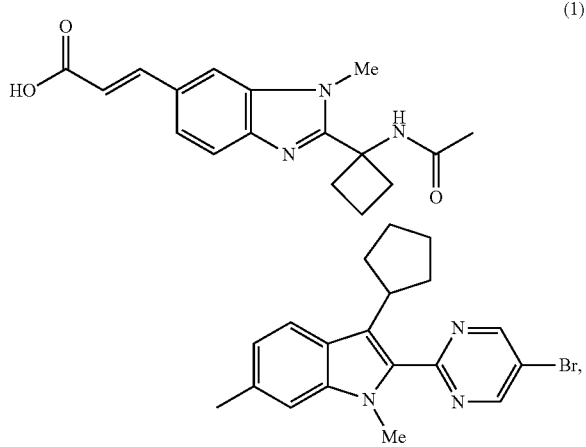

having a $^{13}$C solid state NMR spectrum comprising peaks at chemical shifts of 158.4, 138.3 and 120.2 ppm (±3 ppm).

23. The amorphous sodium salt according to claim 22, having a $^{13}$C solid state NMR spectrum comprising peaks at chemical shifts of 158.4, 142.9, 138.3, 131.5, 128.3, 120.2 and 111.0 ppm (±3 ppm).

24. A pharmaceutical composition comprising the amorphous sodium salt according to claim 22 and at least one pharmaceutically acceptable carrier or diluent.

25. A pharmaceutical composition according to claim 24 comprising
(a) amorphous Compound (1) sodium salt;
(b) at least one surfactant;
(c) at least one basifier;
(d) at least one polymer;
and optionally one or more pharmaceutically acceptable excipients.

26. A pharmaceutical composition according to claim 24 comprising:
(a) 1% to 90% by weight amorphous Compound (1) sodium salt;
(b) 1% to 50% by weight surfactant;
(c) 1% to 50% by weight basifier;
(d) 1% to 99% by weight polymer;
and optionally one or more pharmaceutically acceptable excipients.

27. A pharmaceutical composition according to claim 24 comprising:
(a) 1% to 80% by weight amorphous Compound (1) sodium salt;
(b) 1% to 30% by weight surfactant;
(c) 2% to 40% by weight basifier;
(d) 10% to 80% by weight polymer;
and optionally one or more pharmaceutically acceptable excipients.

28. A pharmaceutical composition according to claim 24 comprising:
(a) 1% to 70% by weight amorphous Compound (1) sodium salt;
(b) 2% to 20% by weight surfactant;
(c) 5% to 20% by weight basifier;
(d) 20% to 70% by weight polymer;
and optionally one or more pharmaceutically acceptable excipients.

29. A pharmaceutical composition according to claim 24 comprising:
(a) 30% to 60% by weight amorphous Compound (1) sodium salt;
(b) 2% to 10% by weight surfactant;
(c) 5% to 15% by weight basifier;
(d) 20% to 40% by weight polymer;
and optionally one or more pharmaceutically acceptable excipients.

* * * * *